US011021723B2

(12) United States Patent
Coleman et al.

(10) Patent No.: US 11,021,723 B2
(45) Date of Patent: Jun. 1, 2021

(54) SYSTEM AND METHOD FOR BIOSYNTHESIS

(71) Applicant: The Regents of the University of California, Oakland, CA (US)

(72) Inventors: Todd Prentice Coleman, La Jolla, CA (US); Marianne Catanho, San Diego, CA (US); Phillip Kyriakakis, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 175 days.

(21) Appl. No.: 16/098,700

(22) PCT Filed: May 4, 2017

(86) PCT No.: PCT/US2017/031165
§ 371 (c)(1),
(2) Date: Nov. 2, 2018

(87) PCT Pub. No.: WO2017/192920
PCT Pub. Date: Nov. 9, 2017

(65) Prior Publication Data

US 2019/0382816 A1 Dec. 19, 2019

Related U.S. Application Data

(60) Provisional application No. 62/331,645, filed on May 4, 2016.

(51) Int. Cl.

| | |
|---|---|
| ***C12P 17/16*** | (2006.01) |
| ***C07K 5/02*** | (2006.01) |
| ***C07K 14/47*** | (2006.01) |
| ***C12N 9/02*** | (2006.01) |
| ***C12P 3/00*** | (2006.01) |
| ***C12P 13/14*** | (2006.01) |

(52) U.S. Cl.
CPC .......... *C12P 17/165* (2013.01); *C07K 5/0215* (2013.01); *C07K 14/4702* (2013.01); *C12N 9/001* (2013.01); *C12N 9/0095* (2013.01); *C12P 3/00* (2013.01); *C12P 13/14* (2013.01); *C12Y 103/07004* (2013.01); *C12Y 103/07005* (2013.01); *C12Y 118/01002* (2013.01)

(58) Field of Classification Search
None
See application file for complete search history.

(56) References Cited

U.S. PATENT DOCUMENTS

| | | | |
|---|---|---|---|
| 6,740,507 B2 | 5/2004 | Glazer et al. | |
| 6,887,688 B2 | 5/2005 | Lagarias et al. | |
| 2003/0027285 A1 | 2/2003 | Glazer et al. | |
| 2003/0073235 A1* | 4/2003 | Lagarias | C12N 15/8261 435/446 |
| 2003/0104379 A1 | 6/2003 | Lagarias et al. | |
| 2016/0237444 A1* | 8/2016 | Nielsen | C12N 9/0008 |

FOREIGN PATENT DOCUMENTS

WO 2013185892 A1 12/2013

OTHER PUBLICATIONS

Shin et al. "Expression of recombinant full-length plant phytochromes assembled with phytochromobilin in Pichia pastoris." FEBS Letters 588.17 (2014): 2964-2970. (Year: 2014).*
Müller et al. "Synthesis of phycocyanobilin in mammalian cells." Chemical Communications 49.79 (2013): 8970-8972. (Year: 2013).*
Schindelin, J. et al. "Fiji: an open-source platform for biological-image analysis" Nature Methods, Jul. 2012, 9(7), 676-682.
Aliverti, A. et al., "Structural and functional diversity of ferredoxin-NADP+ reductases." Archives of biochemistry and biophysics 474.2 (2008): 283-291.
Alvey et al., "Attachment of Noncognate Chromophores to CpcA of *Synechocystis* sp. PCC 6803 and *Synechococcus* sp. PCC 7002 by Heterologous Expression in *Escherichia coli*", Biochemistry, 2011, 50, pp. 4890-4902.
"Chiu, F.-Y. et al., ""Electrostatic interaction of phytochromobilin synthase and ferredoxin for biosynthesis of phytochrome chromophore."" Journal of Biological Chemistry 285.7(2010): 5056-5065."
Frankenberg et al., "Phycocyanobilin: Ferredoxin Oxidoreductase of*Anabaena* sp. PCC 7120 Biochemical and Spectroscopic Characterization.", J. Boil. Chem. 278, 11, 2003, pp. 9219-9226.
Kohchi, T. et al., "The *Arabidopsis* HY2 gene encodes phytochromobilin synthase, a ferredoxin-dependent biliverdin reductase." The Plant Cell 13.2 (2001): 425-436.
Muller et al., "Synthesis of phycocyanobilin in mammalian cells.", Chemical Communications, 49, 2013, pp. 8970-8972.
Rhie et al. Phycobilin biosynthesis: reductant requirements and product identification for heme oxygenase from Cyanidium caldarium; Arch Biochem Biophys, Jun. 20, 1995 (Jun. 20, 1995). vol. 320, pp. 182-194.
Shimizu-Sato, S. et al., "A light-switchable gene promoter system." Nature biotechnology 20.10 (2002): 1041-1044.
International Search Report and Written Opinion for PCT Application No. PCT/US2017/031165, dated Jul. 31, 2017, 7 pages.

* cited by examiner

*Primary Examiner* — Emily A Cordas
(74) *Attorney, Agent, or Firm* — Perkins Coie LLP

(57) ABSTRACT

Methods, systems, and devices are disclosed for in vivo production or biosynthesis of metabolites in foreign cells using the combination of (i) one or more ferredoxin dependent enzyme(s) and (ii) a ferredoxin (Fd)/ferredoxin-NADP$^+$ reductase (FNR) system. The ferredoxin dependent enzymes and the Fd/FNR system are from the same species or from a different but matching species.

23 Claims, 14 Drawing Sheets

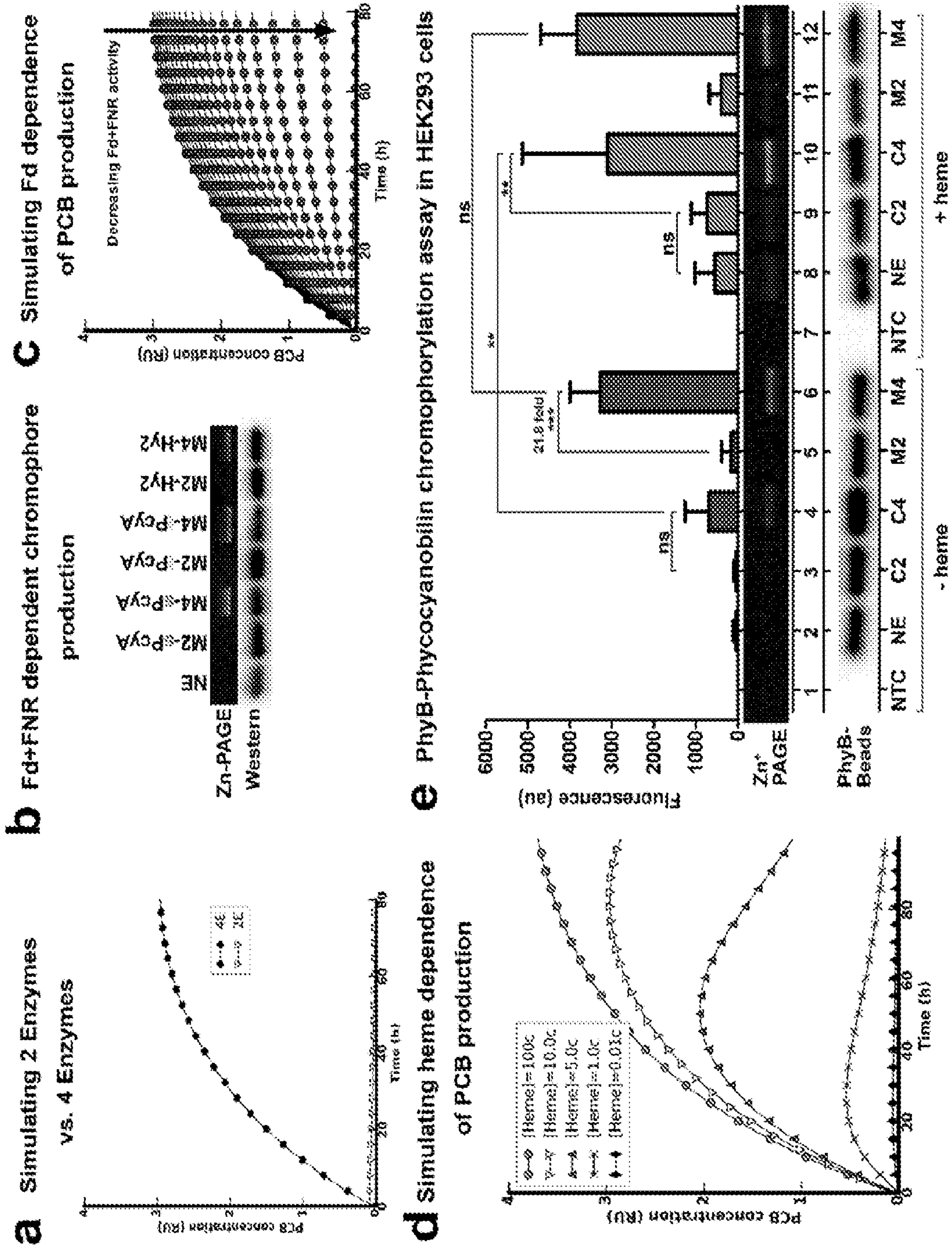

Figure 8
a Simulating 2 Enzymes vs. 4 Enzymes
PCB concentration (RU)
Time (h)
b Fd+FNR dependent chromophore production
Zn-PAGE
Western
NE
M2-ΔPcyA
M4-ΔPcyA
M2-PcyA
M4-PcyA
M2-Hy2
M4-Hy2
c Simulating Fd dependence of PCB production
Decreasing Fd+FNR activity
PCB concentration (RU)
Time (h)
d Simulating heme dependence of PCB production
[Heme]=100c
[Heme]=10.0c
[Heme]=5.0c
[Heme]=1.0c
[Heme]=0.01c
PCB concentration (RU)
Time (h)
e PhyB-Phycocyanobilin chromophorylation assay in HEK293 cells
Fluorescence (au)
ns
21.8 fold
***
**
Zn+ PAGE
PhyB-Beads
NTC
NE
C2
C4
M2
M4
- heme
+ heme Figure 12
a Stoichiometry effects on PCB production
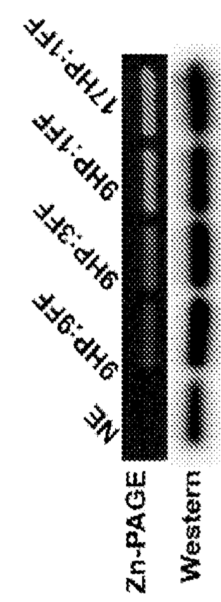
b Stochiometry effects on gene activation
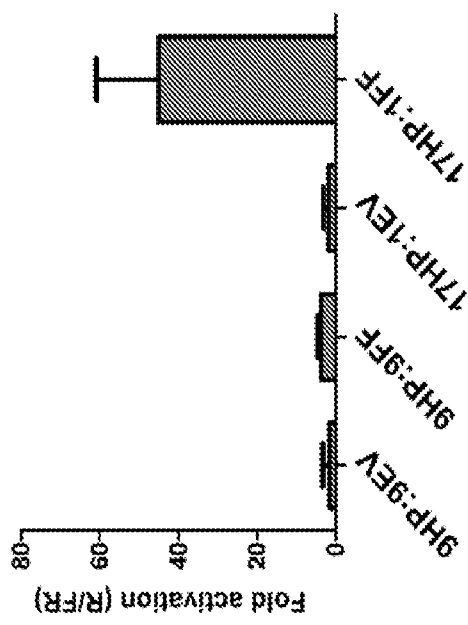
C Lentiviral constructs containing all PCB biosynthetic enzymes
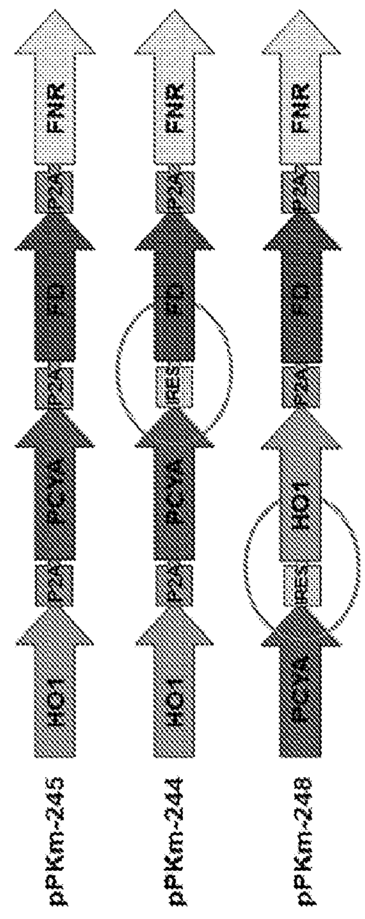
d Single plasmid PCB biosynthesis constructs
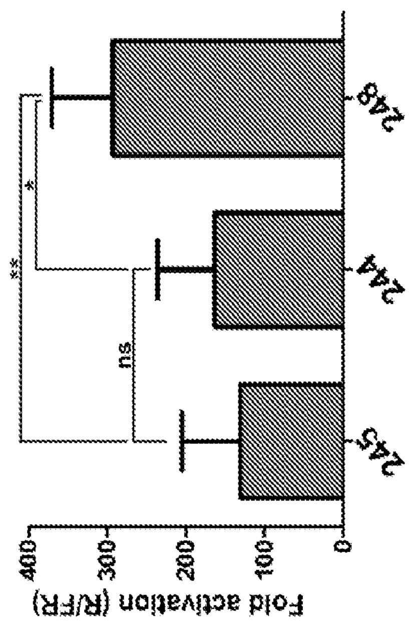

SYSTEM AND METHOD FOR BIOSYNTHESIS

CROSS-REFERENCE TO RELATED APPLICATIONS

This patent document is a 371 National Phase Application of PCT Application No. PCT/US2017/031165 entitled "System and Method for Biosynthesis", filed on May 4, 2017 which claims benefit and priority of U.S. Provisional Patent Application No. 62/331,645 entitled "System and Method for Biosynthesis," filed on May 4, 2016. The entire content of the aforementioned patent applications are incorporated by reference as part of the disclosure of this patent document.

STATEMENT REGARDING FEDERALLY SPONSORED RESEARCH OR DEVELOPMENT

This invention was made with government support under Grant Number CCF-0939370, awarded by National Science Foundation through the NSF Center for Science of Information. The government has certain rights to the invention.

TECHNICAL FIELD

This patent document relates to systems, devices, and processes for biosynthesis of metabolites from plants or cyanobacteria in non-plant or non-cyanobacterial cells, such as vertebrate cells, mammalian cells, including human cells, using plant or cyanobacterial ferredoxin (Fd)/ferredoxin-$NADP^+$ reductase (FNR) systems.

BACKGROUND

Tetrapyrroles are a class of pigments found in certain types of algae and bacteria, in which organisms it is has functions in signaling, soaking up light energy among others. Phycocyanobilin (PCB), a molecule in this class, can easily bind to a protein to form a PCB-protein complex (phycobilin protein). Therefore, PCB is a useful tool for tagging and detecting the presence of molecules and various conditions, drug delivery, photo-activation, imaging, etc. Although it was reported that two biosynthetic enzymes, heme oxygenase-1 (HO) and phycocyanobilin:ferredoxin oxidoreductase (PcyA), were involved in PCB biosynthesis, high level production of PCB in a non-plant or non-bacterial, higher system, such as insect or mammalian system, was not achieved. The technology described in this disclosure satisfies the needs in the art.

SUMMARY

Techniques, systems, and devices are disclosed for implementing a fully endogenous and efficient production of metabolites from one kingdom of life in a species from another.

The subject matter described in this patent document can be implemented in specific ways that provide one or more of the following features. For example, it can significantly increase production of cyanobacterial (a type of bacteria) metabolites in animal cells, e.g., by over twenty-fold. These metabolites can be used for imaging, controlling biological processes with light, such as genes or protein localization and more.

In one aspect, this disclosure relates to a system of in vivo production of a metabolite in a foreign host cell. The system includes: (i) one or more ferredoxin dependent enzymes targeting a specific subcellular location such as cytoplasm, mitochondria, peroxisome, or other organelles that can be targeted genetically; and (ii) a ferredoxin (Fd)/ferredoxin-NADP+ reductase (FNR) system (Fd-FNR system) targeting the same specific subcellular location, wherein the metabolite and the one or more ferredoxin dependent enzymes are from the same species, the metabolite and the host cell are from different species, and the Fd/FNR system and the one or more ferredoxin dependent enzymes are from the same species. In some embodiments, a bacterial metabolite is in vivo produced in an animal or plant cell. In other embodiments, a plant metabolite is in vivo produced in an animal or bacterial cell. In some embodiments, the host cell includes a bacterial cell, a plant cell, an animal cell, a vertebrate cell, and a human cell. In some embodiments, the system includes two or more ferredoxin dependent enzymes. In some embodiments, the ferredoxin dependent enzyme includes phycocyanobilin and phytochromobilin synthesis enzymes. In some embodiments, the ferredoxin dependent enzyme includes HO1, PcyA, and/or Hy2. In some embodiments, the metabolite includes phycocyanobilin, phytochromobilin, a steroid, ammonia, glutathione, thioredoxin and glutamate.

In a related aspect, this disclosure relates to a method of in vivo producing a metabolite in a foreign host cell. The method entails (i) providing to the foreign host cell (a) one or more ferredoxin dependent enzymes targeting a specific subcellular location such as cytoplasm, mitochondria, peroxisome, or other organelles that can be targeted genetically, and (b) a ferredoxin (Fd)/ferredoxin-NADP+ reductase (FNR) system (Fd-FNR system) targeting the same specific subcellular location, and (ii) culturing the host cell such that the metabolite is produced in the host cell, wherein the metabolite and the one or more ferredoxin dependent enzymes are from the same species, the metabolite and the host cell are from different species, and the Fd/FNR system and the one or more ferredoxin dependent enzymes are from the same species. In some embodiments, a bacterial metabolite is in vivo produced in an animal or plant cell. In other embodiments, a plant metabolite is in vivo produced in an animal or bacterial cell. In some embodiments, the host cell includes a bacterial cell, a plant cell, an animal cell, a vertebrate cell, and a human cell. In some embodiments, the system includes two or more ferredoxin dependent enzymes. In some embodiments, the ferredoxin dependent enzyme includes phycocyanobilin and phytochromobilin synthesis enzymes. In some embodiments, the ferredoxin dependent enzyme includes HO1, PcyA, and/or Hy2. In some embodiments, the metabolite includes phycocyanobilin, phytochromobilin, a steroid, ammonia, glutathione, thioredoxin and glutamate. In some embodiments, the DNA encoding the one or more ferredoxin dependent enzymes is transduced or transfected into the host cell such that the DNA is expressed in the host cell. In some embodiments, the DNA encoding the one or more ferredoxin dependent enzymes is co-transduced or co-transfected with the DNA encoding the Fd-FNR system.

In another aspect, this disclosure relates to a system of in vivo production of a metabolite in a foreign host cell. The system includes: (i) one or more ferredoxin dependent enzymes targeting a specific subcellular location such as cytoplasm, mitochondria, peroxisome, or other organelles that can be targeted genetically; and a ferredoxin (Fd)/ferredoxin-NADP+ reductase (FNR) system (Fd-FNR system) targeting the same specific subcellular location, wherein the metabolite and the one or more ferredoxin dependent enzymes are from the same species, the metabolite and the host cell are from different species, the Fd/FNR system and the one or more ferredoxin dependent enzymes are from the different species, and the amino acid sequence of the ferredoxin of the species of the one or more ferredoxin dependent enzymes and the amino acid sequence of the ferredoxin of the Fd/FNR species are at least 40%, at least 50%, at least 60%, at least 70%, at least 80%, at least 90%, at least 95%, or 100% identical. In this aspect, the Fd/FNR system and the one or more ferredoxin dependent enzymes are from different but "matching" species. In the context of this disclosure, "matching" is determined by comparing the amino acid sequence of the ferredoxin of one species to the amino acid sequence of the ferredoxin of another species, where at least 40%, at least 50%, at least 60%, at least 70%, at least 80%, at least 90%, at least 95%, or 100% identity in the amino acid sequence indicates that the species match. In some embodiments, a bacterial metabolite is in vivo produced in an animal or plant cell. In other embodiments, a plant metabolite is in vivo produced in an animal or bacterial cell. In some embodiments, the host cell includes a bacterial cell, a plant cell, an animal cell, a vertebrate cell, and a human cell. In some embodiments, the system includes two or more ferredoxin dependent enzymes. In some embodiments, the ferredoxin dependent enzyme includes phycocyanobilin and phytochromobilin synthesis enzymes. In some embodiments, the ferredoxin dependent enzyme includes HO1, PcyA, and/or Hy2. In some embodiments, the metabolite includes phycocyanobilin, phytochromobilin, a steroid, ammonia, glutathione, thioredoxin and glutamate.

In a related aspect, this disclosure relates to a method of in vivo producing a metabolite in a foreign host cell. The method entails (i) transplanting into a foreign host cell (a) one or more ferredoxin dependent enzyme(s) targeting a specific subcellular location such as cytoplasm, mitochondria, peroxisome, or other organelles that can be targeted genetically, and (b) an Fd-FNR system targeting the same specific subcellular location, and (ii) culturing the transplanted host cell such that the metabolite is produced in the host cell, wherein the metabolite and the one or more ferredoxin dependent enzymes are from the same species, the metabolite and the host cell are from different species, the Fd/FNR system and the one or more ferredoxin dependent enzymes are from different species, and the amino acid sequence of the ferredoxin of the species of the one or more ferredoxin dependent enzymes and the amino acid sequence of the ferredoxin of the Fd/FNR species are at least 40%, at least 50%, at least 60%, at least 70%, at least 80%, at least 90%, at least 95%, or 100% identical. In this aspect, the Fd/FNR system and the one or more ferredoxin dependent enzymes are from different but "matching" species. In the context of this disclosure, "matching" is determined by comparing the amino acid sequence of the ferredoxin of one species to the amino acid sequence of the ferredoxin of another species, where at least 40%, at least 50%, at least 60%, at least 70%, at least 80%, at least 90%, at least 95%, or 100% identity in the amino acid sequence indicates that the species match. In some embodiments, a bacterial metabolite is in vivo produced in an animal or plant cell. In other embodiments, a plant metabolite is in vivo produced in an animal or bacterial cell. In some embodiments, the host cell includes a bacterial cell, a plant cell, an animal cell, a vertebrate cell, and a human cell. In some embodiments, the system includes two or more ferredoxin dependent enzymes. In some embodiments, the ferredoxin dependent enzyme includes phycocyanobilin and phytochromobilin synthesis enzymes. In some embodiments, the ferredoxin dependent enzyme includes HO1, PcyA, and/or Hy2. In some embodiments, the metabolite includes phycocyanobilin, phytochromobilin, a steroid, ammonia, glutathione, thioredoxin and glutamate.

In another aspect, this disclosure relates to a method of utilizing the biological activity of the metabolites from a different species for imaging. This method entails transfecting the DNA encoding the metabolic pathway for metabolite production along with proteins that bind the metabolite, incubating to allow biosynthesis and then imaging the location of the metabolite bound protein by imaging the fluorescent metabolite using fluorescence microscopy.

In another aspect, this disclosure relates to a method of controlling the biological activity with light using a metabolite from a different species. This method entails transfecting the DNA encoding the metabolic pathway for metabolite production along with proteins that bind the metabolite and subsequently become light responsive proteins, then shining light to active or deactivate genes.

BRIEF DESCRIPTION OF THE DRAWINGS

FIG. 6A: PhyB-NLS alone did not fluoresce. FIG. 6B: PhyB-NLS bound PCB fluorescence, 10 μM PCB was added to cells one hour prior to fixing cells. FIG. 6C: Endgenous PCB production using PcyA+HO1 with the Fd-FNR system.

FIG. 8 shows rate limiting factors of PCB production. FIG. 8*a*: Simulation of PCB synthesis with (circle, black) and without (triangle, white) the NADPH/FNR/Fd redox cascade. FIG. 8*b*: Zn-PAGE gel analyzing PCB production using three species of Ferredoxin-dependent Bilin reductases (FdBRs) localized to the mitochondria with the FdBRs alone (M2) or with Fd+FNR (M4). FIG. 8*c*: Simulation of PCB production with decreasing Fd-FNR activity. FIG. 8C: Simulation of PCB production with decreasing Fd-FNR activity. FIG. 8*d*: Simulation of PCB production with decreasing heme. FIG. 8*e*: Zn-PAGE gel analyzing PCB production, comparing cytoplasmic expression with PcyA+HO1 alone (C2) with cytoplasmic PcyA+HO1+Fd+FNR (C4), mitochondrial expression with PcyA+HO1 alone (M2) with mitochondrial PcyA+HO1+Fd+FNR (M4), without (−heme) and with (+heme) excess heme. NTC—Non Transfected Control, NE=No Enzymes. (One-way ANOVA with Bonferroni post-test was used to calculate p values GraphPad Prism 5.01. (*)=$p<0.001$, ()=$p<0.01$, Error bars=Standard Deviation (s.d.), n=4 independent experiments).

FIG. 11*a*: Schematic of the PhyB-PIF3 light switch. PhyB is fused to a DNA Binding Domain (DBD) and bound to a light sensitive chromophore (PCB). The PhyB-DBD fusion remains bound to the UAS promoter. PIF3 is fused to an Activation Domain (AD). Upon absorption of a red photon (650 nm), PhyB changes conformation and recruits to PIF3 to the promoter region. The AD fused to PIF3 then activates the gene downstream of the promoter. Upon absorption of a farred photon (740 nm), PhyB changes conformation leading to PIF3 unbinding, removing the AD from the promoter, shutting the downstream gene off. FIG. 11*b*: Comparison of gene activation using several variations of the light switch. The negative control consists of UAS-luciferase plasmid alone. In the first two conditions, PIF6 or PIF3 are fused to the DBD (P6-DBD and P3-DBD, respectively) and PhyB with fused to the AD (PhyB-AD). The second two conditions contain PhyB fused to the DBD along with PIF6 and PIF3 fused to the AD (P6-AD and PIF3-AD, respectively). 15 μM PCB was exogenously added to test gene activation of the switch (n=6, Error bars=s.d.). FIG. 11*e*: Comparison of MTAD and VPR activation domains and C-terminal or N-terminal AD fusions onto PIF3 using 10M PCB (n=3, Error bars=s.d.) FIG. 11*d*: Leakiness analysis comparing different reporter vectors. HEK293 cells were transfected with the reporter vector with *Renilla* (pPKm-121) or with *Renilla*+mOrange (pPKm-121, pPKm-102) plasmid. Luciferase values were normalized to *Renilla* (n=5, Error bars=s.d.). Figure lie: Activation level comparison of Gal4-UAS reporters. HEK293 cells transfected with Fluc-UAS and CMV-UAS along with Gal4-VP16 (n=3, Error bars=s.d.).

FIG. 12 shows optimizing PCB production constructs. FIG. 12*a*: Comparing several ratios of PcyA+HO1 to Fd-FNR using a Zn-PAGE gel and Western Blot to analyze PCB production. FIG. 12*b*: Comparing gene activation levels under several ratios of PcyA+HO1 to Fd-FNR using a luciferase assay (n=3, Error bars=s.d.). FIG. 12*c*: Maps of constructs consisting of all four biosynthetic enzymes on a single plasmid. FIG. 12*d*: Comparison of light induced luciferase gene expression using PCB biosynthetic plasmids pPKm-245, pPKm-244 and pPKm-248 (n=7, Error bars=s.d., (*)=$p<0.05$, (**)=$p<0.01$. Statistics were calculated using one-way ANOVA with Bonferroni post-test with GraphPad Prism 5.01).

FIG. 13*a*: RAGS light sensitivity through photon counts. HEK293 cells where transfected with 244 RAGS or 248 RAGS and continuous 1 mole/$m^2$/sec or pulsing 0.1 μmole/$m^2$/sec red light with different time intervals for 24 hours. Cont=continuous illumination, 1/4=one minute red light, 4 minutes darkness, 1/9=one minute red light, 9 minutes darkness, 1/29=one minute red light, 29 minutes darkness (n=3, Error bars=s.d.). FIG. 13*b*: HEK293 cells transfected with RAGS to test reversibility. Cells were in darkness, illuminated with far red light for 24 hours, red light for 24 hours, or with 12 hours or red light followed by darkness or followed by far-red light (n=3, Error bars=s.d.). FIG. 13*c*: Testing the duration of activation. Cells were pulsed for one minute using 1 μmole/$m^2$/sec light, followed by darkness for the indicated times. Cells were pusled for a total of 24 hours. (n=5, Error bars=s.d.). FIG. 13*d*: Testing RAGS in four different cell types. Cells were transfected with RAGS and then illuminated with red light for 24 hours. (n=4, Error bars=s.d., (*)=$p<0.05$, statistics were calculated using one-way ANOVA with Bonferroni post-test with GraphPad Prism 5.01).

DETAILED DESCRIPTION

Techniques, systems, and devices are described for biosynthesis of plant and bacterial metabolites in non-plant or non-bacterial cells. Many of these metabolites can be used as biologically active agents, such as drugs, or as a photosensitizer/imaging.

The technology described in this disclosure relates to how genes encoding ferredoxin dependent biosynthetic enzymes are transferred from one species into a host cell of a different species to produce ferredoxin dependent metabolites. Matching ferredoxin (Fd) and ferredoxin-NADP+-reductase (FNR) reduction (Fd+FNR) with the ferredoxin-dependent enzymes allows for the production of metabolites not normally produced in that cell type. For example, the disclosed technology can be used for the production of many plant and cyanobacterial metabolites in mammalian cells, or for introducing metabolic pathways from one species to another.

Fd-FNR is a Rate Limiting System for Transplanting Metabolic Pathways

Figure 14:
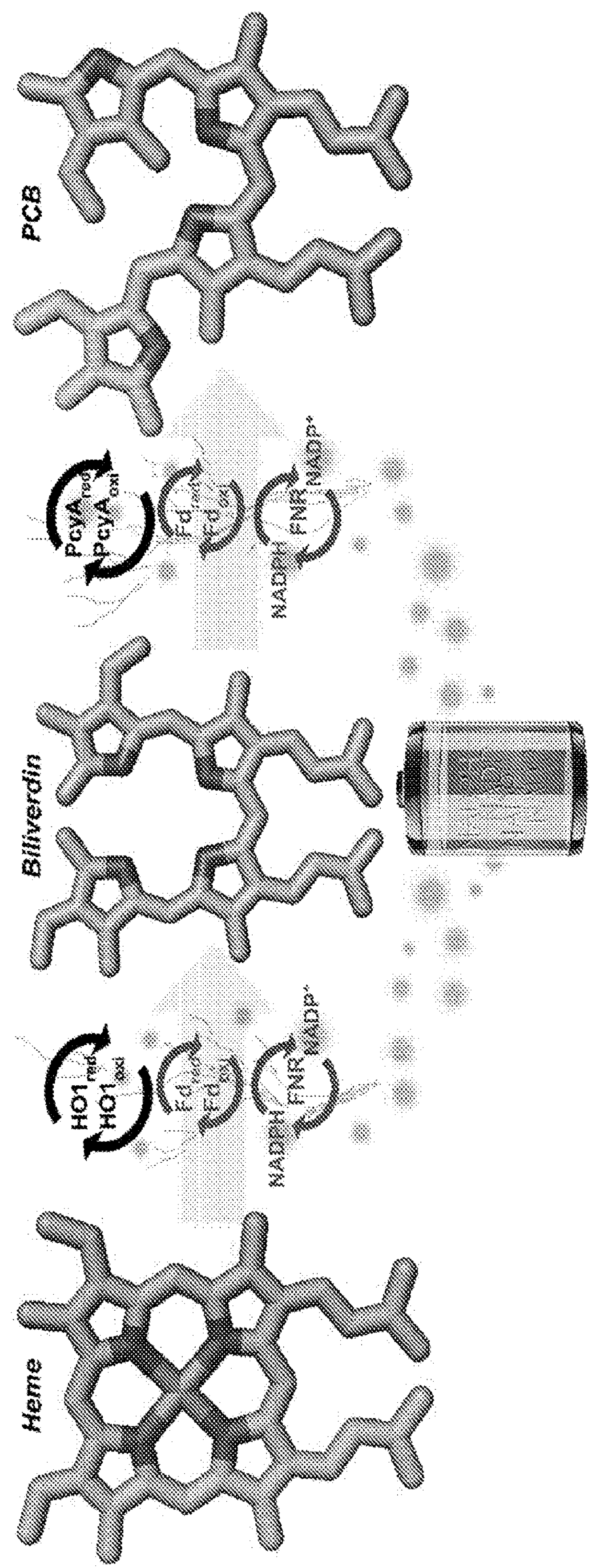
FIG. 14 illustrates the concept of Fd-FNR supplying electrons into a metabolic pathway. While the Fd-FNR system doesn't participate directly on the metabolite reactions, the system supplies electrons that recycle the enzymes in the pathway. If the host cell's Fd-FNR system does not efficiently recycle the enzymes in the transplanted metabolic pathway, production of metabolites in the host cell will be limited. Matching the Fd-FNR system to the transplanted pathway ensures that electron supplies will not be limiting, maximizing production through the transplanted metabolic pathway.

Disclosed herein is a system of in vivo producing or biosynthesizing a metabolite in non-native species. The system includes one or more ferredoxin-dependent biosynthetic enzymes targeting a specific subcellular location, and a ferredoxin (Fd)/ferredoxin-NADP+ reductase (FNR) system from an different species. As demonstrated in the working examples, the Fd+FNR system is the rate limiting factor for efficient production of the bacterial and plant metabolites PCB and PΦB respectively, in mammalian cells. The ability to produce PCB and POB with distinct enzymes PcyA and Hy2, respectively, indicates that production of other bilins and other classes of metabolites can be limited by the host's Fd-FNR system. This means that metabolites can be more efficiently produced through matching reduction systems (Fd-FNR) that efficiently supply electrons to the pathway. Matching Fd-FNR to the transplanted metabolic pathway more efficiently supplies electrons to that pathway from the cells energy source than the host cell's Fd-FNR system. Matching an Fd-FNR system to the transplanted metabolic pathway can be analogized as supplying wires to power transplanted metabolic pathways, which boosts production of a desired metabolite (Illustrated in FIG. 14).

It was previously demonstrated in vitro that Fd activity on PcyA from *Anabaena* sp. PCC 7120 varies greatly depending on the Fd species. Because mammalian Fds have also been shown to be highly substrate- and tissue-specific, it was possible that mammalian Fds may not be efficient replacements for cyanobacterial or plant Fds and that the host cell's Fd is rate limiting for metabolite production. This remained untested in a cell and may be important for the production of many plant and bacterial metabolites in other cells, or generally when transplanting metabolic pathways from one species to another. Using PCB and PΦB as examples, the working examples demonstrate that by species matching the Fd+FNR system, it is possible to produce over one order of magnitude higher levels of metabolites compared to relying on endogenous Fd+FNR. This highlights the importance of the finding that the availability of electrons in the biosynthetic pathway are important considerations in synthetic biology.

It was shown that HO1 and PcyA were sufficient to produce PCB in bacterial and plant systems (see U.S. Pat. Nos. 6,887,688 and 6,740,507). However, in these experiments, the ferredoxin or Fd-FNR system was not transplanted along with HO1 and PcyA. In those species, the addition of the native or similar ferredoxin system is not required for detectable production levels, but they too can be improved by the addition of a matching Fd-FNR system. Whether or not Fd-FNR was limiting in cells was not tested. Plant and cyanobacterial ferredoxin reductase systems are evolutionarily diverged from animal types and bacterial types. It is shown in this disclosure that Fd-FNR systems from that plants or bacteria is limiting and that transplanting the metabolic pathway donor's Fd-FNR system are required to have enzymes like PcyA have high efficiency production. It is demonstrated herein beyond in vitro experiments, that in cells, Fd-FNR is rate limiting when transplanting pathways from one species to another.

Figure 5:
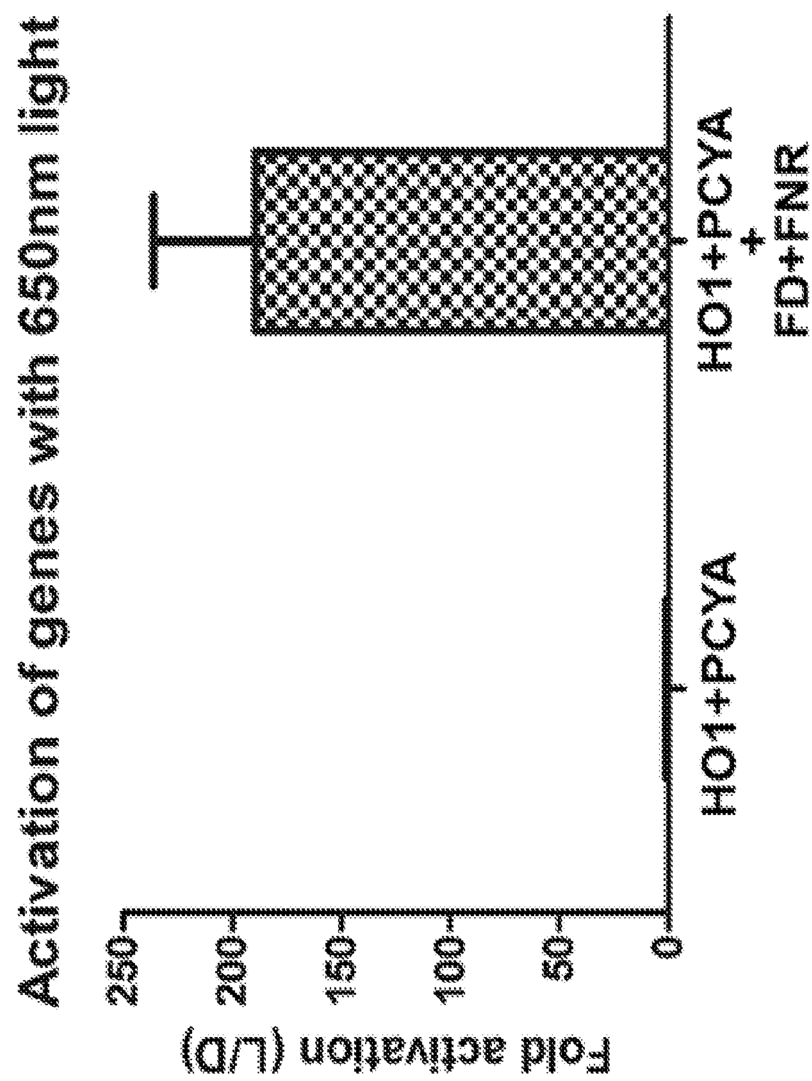
FIG. 5 shows that the Fd+FNR system is required for the PhyB-PIF3 gene-switch to function without exogenous addition of a chromophore. HO1 and PcyA alone were not sufficient for any response from red light, whereas addition of Fd+FNR lead to 180 fold (light/dark, L/D) response to 650 nm/red light. This also demonstrates the bioactivity of endogenously produced PCB.
Figure 11:
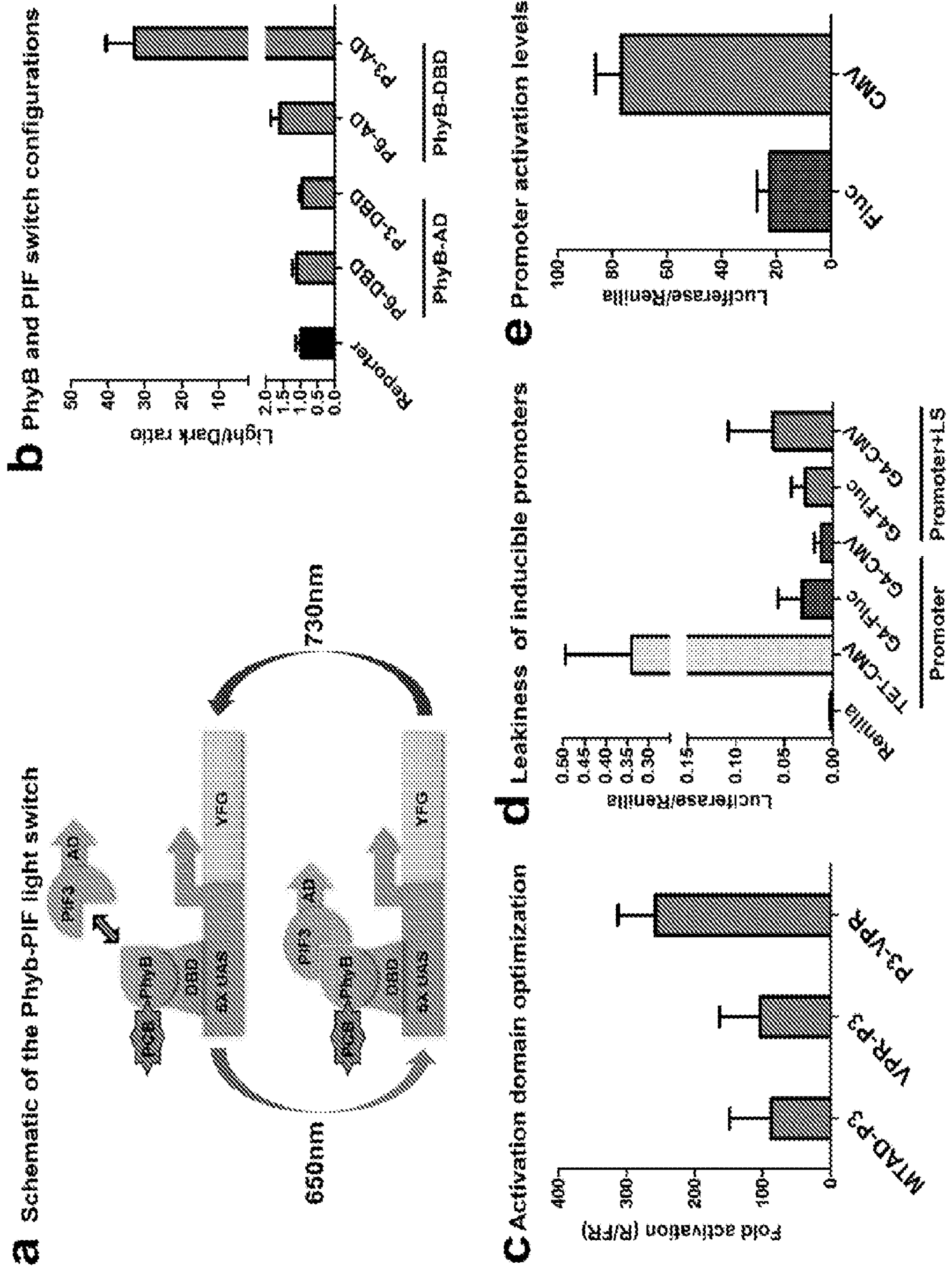
FIG. 11 illustrates optimizing PhyB and PIF gene switch.

Although Müller et al., *Chemical Communications* 49 (79): 8970-8972 (2013) expressed two PCB biosynthetic enzymes HO1 and PcyA and shone light in an attempt to activate genes, PCB production was not disclosed. As shown in the working examples, the expression of HO1+PcyA alone did not produce PCB when assayed by testing through a similar, but more sensitive gene expression assay, than in Müller et al. (FIGS. 5 and 11B). Additionally, it is the addition of the Fd-FNR system that allows for high levels production of PCB by directly measuring PCB in a gel and using microscopy. Further, the system disclosed herein allows for the production of an additional metabolite (phytochromobilin (PφB)) from a plant cell in an animal cell. There are many ferredoxin dependent reactions in evolution.

It is demonstrated in this disclosure that (1) the Fd/FNR system can be limiting for producing bacterial or plant metabolites in non-plant or non-bacterial cells, (2) that reintroducing the Fd+FNR, natively used by the Fd or FNR dependent process, removes the bottleneck and drastically increases bioproduction, and (3) the system can be used to control biological processes, such as, but not limited to genes.

In certain embodiments, the Fd/FNR system disclosed herein contains a heterologous Fd and/or a heterologous FNR. In some embodiments, the Fd and/or FNR species matches or is compatible to the Fd dependent cellular process exogenously produced. In some embodiments, only Fd or only FNR is not matching and only Fd or FNR are transplanted.

As demonstrated in the working examples, this disclosure exemplifies biosynthesis of other metabolites. For example, *Arabidopsis* Hy2 was used to produce phytochromobilin (PφB) instead of PCB. The working examples further demonstrate that sufficient Fd/FNR system activity is required for biosynthesis of the metabolites. Using three different sets of ferredoxin-dependent enzymes from bacteria and plants, the endogenous ferredoxin system of mammalian cells was limiting for production of metabolites such as PCB. Other animal systems are also not matching compared to bacterial or plants, since they are evolutionarily similar compared to bacterial and plant type Fd/FNR systems.

Thus, the disclosure demonstrates that the ability to produce the cyanobacterial metabolite phycocyanobilin (PCB) and phycobilin-proteins in mammalian cells is limited by the Fd/FNR system. This disclosure also demonstrates that the ability to produce the plant metabolite phycochromobilin (PyB) and phycobilin-proteins in mammalian cells is limited by the Fd/FNR system.

Matching Systems

Matching means that the ferredoxin-dependent enzyme(s) and the Fd-FNR system are from the same species or a different but "matching" species. To determine "matching" species, the amino acid sequences of ferredoxins from two different species are compared, where at least 40% identity in the amino acid sequences of ferredoxins indicates that these species are matching. In some embodiments, matching means structural similarities. These structures are ultimately determined by the amino acid sequence. However, in the case that different arrangement of amino acids form similar structures, the molecular structure can be determined by X-ray crystallography, Small Angle X-Ray Scattering, Small angle Neutron scattering, NMR, circular dichroism, electron microscopy or other methods. The structure of interface between the host cell's Fd and the transplanted Fd-dependent enzyme are of particular importance when determining if a system is matching. If by comparing structures, the interface between the host cell's Fd and the transplanted Fd-dependent enzyme are not complimentary (binding too strongly or weakly), transplanting the matching Fd-FNR system may be preferred (i.e. the binding interface is not conserved). This can be determined using docking software, molecular dynamics or similar modeling techniques. Binding or binding affinity may also be tested in vitro using a number of methods, such as 2-hybrid systems, surface plasmon resonance, gel shift assays, protein pull down assays and others. The Fd-FNR activity of the host cell's Fd-FNR system can also be tested in vitro/biochemically directly on the biosynthetic pathway to be transplanted and compared to the transplanted pathway using the donor cell's Fd-FNR system. One can determine matching by purifying the host species and the donor species Fd-FNR system and producing metabolites in vitro. Metabolic activity in vitro can be measured by measuring the amount of resulting metabolites using techniques suitable for testing the specific metabolite, such as fluorescence, chromatography, mass spectrometry, NMR etc. If the difference is significant biochemically, then it can be tested in the cell as in this study. If the difference is not significant, then the host Fd-FNR system is already matching.

There are also different classes of Fd's and FNRs. For example, 2Fe-2S, Fe4S4, Fe3S4 types. There are also specialized types depending on subcellular localization (for example, mitochondrial versus chloroplastic, Tables 1B and 1C). The mitochondrial Fd's from *Arabidopsis* are more similar to mitochondrial Fd's in yeast and humans than chloroplastic Fd's in *Arabidopsis*. Due to the shared evolutionary origin of mitochondria and different origin of chloroplast, similarity in mitochondria type Fd's in yeast, plants and animals is expected.

Matching can also be defined by the redox potential. If the host cell's Fd has too low potential compared to the transplanted Fd dependent enzyme, it will not reduce the enzyme. In such cases, transplanting the matching Fd-FNR system will be required for efficient production of metabolites in the host cell.

Figure 3:
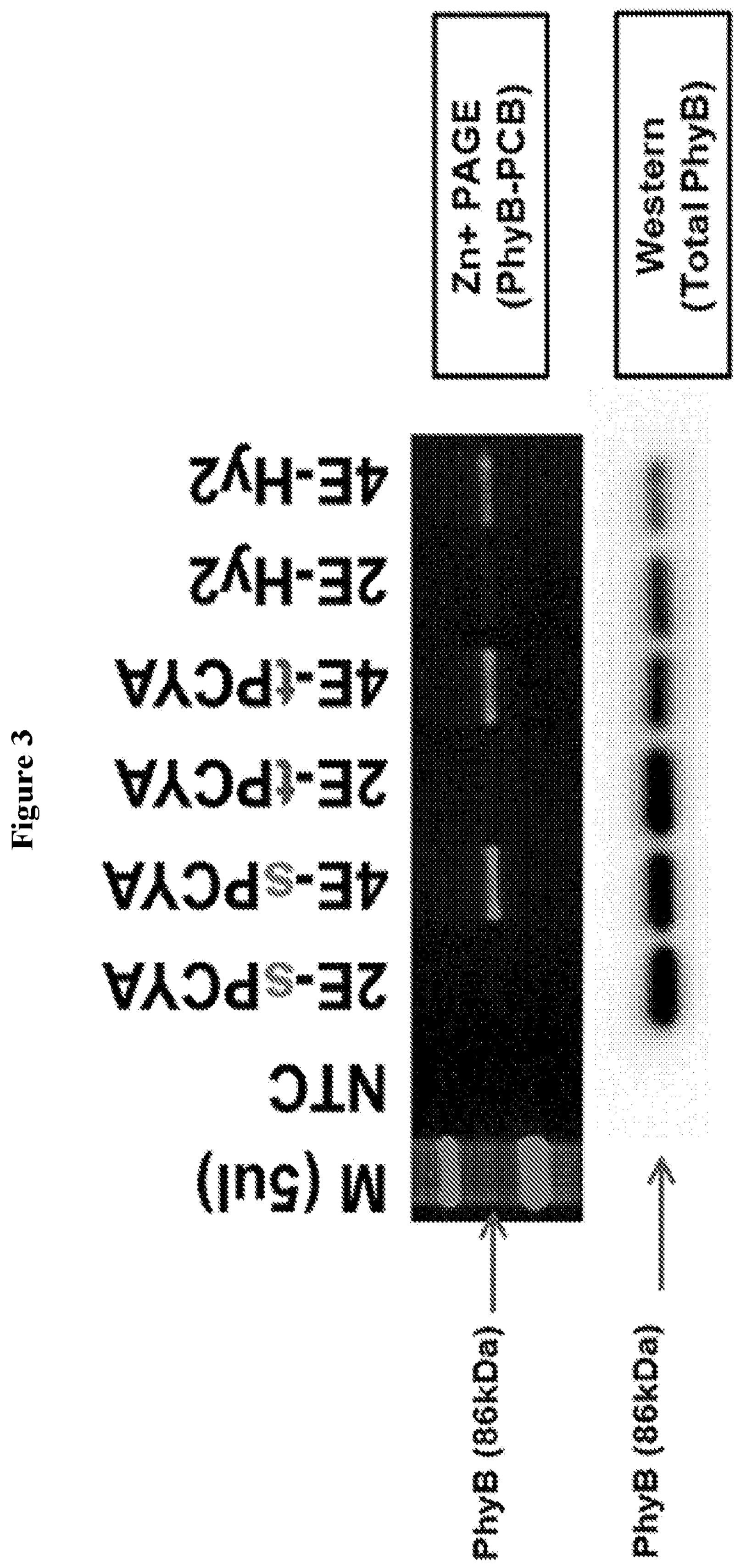
FIG. 3 shows that several species of enzymes require an exogenous Fd+FNR system for activity. Zn-PAGE shows that two species of PcyA ("sPCYA" for *Synechococcus* sp. And "tPCYA" for *Thermosynechococcus elongatus*) produces PCB and using the bacterial Fd-FNR system, the plant Hy2 (*Arabidopsis thaliana*) enzyme produces phytochromobilin (PφB), another biolocially active metabolite/molecule.

Often these differences can be predicted based on the amino acid sequence similarity. For example, in tables 1A, 1B and 1C demonstrate matching and unmatching systems. FIG. 5A shows that even though PcyA and Hy2 come from different Kingdoms, the sequence similarity between the bacterial and plant enzymes (PcyA vs Hy2) are very different than the difference between the two species of bacteria (THEEB PcyA vs Syn-PcyA) [W/SS=with signal sequence, W/O SS=without signal sequence. Signal sequences target enzymes to mitochondria or chloroplasts]. Although the plant type and bacterial type are more similar than the human type, sequence similarity of the Fd instead of the ferredoxin dependent enzyme can also be used to determine matching and can be more informative. Tables 1B and 1C show amino acid sequence similarities of several ferredoxins. In darker grey are the species used to test matching species. Ferredoxin (FER2_ARATH) from *Arabidopsis* is the Fd that reduces Hy2 in *Arabidopsis*. Compared to the human Fd's, both cyanobacterial and plant Fd's are more similar. Before removing the signal sequence (Table 1B), the cyanobacterial and plant Fd's are approximately 40% similar or higher, whereas the highest similarity between plant or bacterial Fd's with human Fd's is approximately 17.9%. After removing the signal sequence (Table 1C), the cyanobacterial and plant Fd's are approximately 59% similar or higher, whereas the highest similarity between plant or bacterial Fd's with human Fd's is approximately 18.3%. In the study, the cyanobacterial Fd was used to reduce the plant enzyme Hy2. This greatly increased metabolite production (FIGS. 3 and 8B). As an approximate rule, the metabolic donor species may be better than the host's Fd. However, if an Fd from a third species or a mutant Fd is shown to better reduce the Fd dependent enzyme, it can be transplanted along with the Fd dependent metabolic pathway. This can be to produce more metabolites, or to minimize expression levels of Fds.

TABLE 1A

Similarity of Ferredoxin-dependent Bilin Reductases and similarity of Fds
Ferredoxin-dependent Bilin Reductases

| | W/SS ARATH-Hy2 | W/OSS ARATH-Hy2 | THEEB-PCYA | Syn-PCYA | human |
|---|---|---|---|---|---|
| W/SS ARATH-Hy2 | | | | | |
| % Identity | | 86.322 | 14.454 | 8.627 | 13.99 |
| Identical AA | | 284 | 49 | 49 | 54 |
| Similar AA | | 0 | 82 | 89 | 95 |

TABLE 1A-continued

Similarity of Ferredoxin-dependent Bilin Reductases and similarity of Fds Ferredoxin-dependent Bilin Reductases

| | W/SS ARATH-Hy2 | W/OSS ARATH-Hy2 | THEEB-PCYA | Syn-PCYA | human |
|---|---|---|---|---|---|
| W/OSS ARATH-Hy2 | | | | | |
| % Identity | 86.322 | | 15.667 | 15.282 | 13.636 |
| Identical AA | 284 | | 47 | 46 | 48 |
| Similar AA | 0 | | 80 | 88 | 87 |
| THEEB-PCYA | | | | | |
| % Identity | 14.454 | 15.667 | | 55.738 | 10.256 |
| Identical AA | 49 | 47 | | 136 | 36 |
| Similar M | 82 | 80 | | 49 | 74 |
| Syn-PCYA | | | | | |
| % Identity | 8.627 | 15.282 | 55.738 | | 9.449 |
| Identical AA | 49 | 46 | 136 | | 36 |
| Similar AA | 89 | 88 | 49 | | 53 |
| human | | | | | |
| % Identity | 13.99 | 13.636 | 10.256 | 9.449 | |
| Identical AA | 54 | 48 | 36 | 36 | |
| Similar AA | 95 | 87 | 74 | 53 | |

TABLE 1B

| Similarity of ferredoxins with eukaryotic sequences containing signal sequences | | | | | | | | | | | |
|---|---|---|---|---|---|---|---|---|---|---|---|
| | THEEB | SYNP2 | FER1_ARATH | FER2_ARATH* | FER3_ARATH | FER4_ARATH | MFDX1_ARATH | MFDX2_ARATH | ADRX_YEAST | ADX_HUMAN | FDX2_HUMAN |
| THEEB | | | | | | | | | | | |
| % Identity | 100 | 71.429 | 39.597 | 39.597 | 40.645 | 32.432 | 12.563 | 13.568 | 15.517 | 10.811 | 12.973 |
| Identical AA | 98 | 70 | 59 | 59 | 63 | 48 | 25 | 27 | 27 | 20 | 24 |
| Similar AA | 0 | 16 | 26 | 26 | 25 | 31 | 37 | 37 | 31 | 37 | 36 |
| SYNP2 | | | | | | | | | | | |
| % Identity | 71.429 | 100 | 42.568 | 44.595 | 40.645 | 40.645 | 12.183 | 9.645 | 16.000 | 11.17 | 12.5 |
| Identical AA | 70 | 97 | 63 | 66 | 63 | 63 | 24 | 19 | 28 | 21 | 23 |
| Similar AA | 16 | 0 | 23 | 20 | 23 | 23 | 35 | 40 | 28 | 37 | 32 |
| FER1_ARATH | | | | | | | | | | | |
| % Identity | 39.597 | 42.568 | 100 | 86.486 | 50 | 45.638 | 20.812 | 15.92 | 18.994 | 16.23 | 19.565 |
| Identical AA | 59 | 63 | 145 | 128 | 78 | 68 | 41 | 32 | 34 | 31 | 36 |
| Simiar AA | 26 | 23 | 0 | 14 | 40 | 44 | 47 | 65 | 49 | 55 | 48 |
| FER2_ARATH* | | | | | | | | | | | |
| % Identity | 39.597 | 44.595 | 86.486 | 100 | 47.436 | 44.295 | 20.202 | 17.588 | 16.949 | 17.617 | 17.857 |
| Identical AA | 59 | 66 | 128 | 148 | 74 | 66 | 40 | 64 | 30 | 34 | 35 |
| Simlar AA | 26 | 20 | 14 | 0 | 46 | 45 | 53 | 35 | 50 | 44 | 46 |
| FER3_ARATH | | | | | | | | | | | |
| % Identity | 40.645 | 40.645 | 50.000 | 47.436 | 100.000 | 41.667 | 17.778 | 20.000 | 19.022 | 18.135 | 17.949 |
| Identical AA | 63 | 63 | 78 | 74 | 155 | 65 | 37 | 40 | 35 | 35 | 35 |
| Similar AA | 25 | 23 | 40 | 46 | 0 | 49 | 54 | 59 | 44 | 57 | 49 |
| FER4_ARATH | | | | | | | | | | | |
| % Identity | 32.432 | 40.645 | 45.638 | 44.295 | 41.667 | 100.000 | 13.065 | 17.413 | 19.886 | 15.426 | 12.821 |
| Identical AA | 48 | 63 | 68 | 66 | 65 | 148 | 26 | 35 | 35 | 29 | 25 |
| Similar AA | 31 | 23 | 44 | 45 | 49 | 0 | 59 | 51 | 50 | 57 | 53 |
| MFDX1_ARATH | | | | | | | | | | | |
| % Identity | 12.563 | 12.183 | 20.812 | 20.202 | 17.778 | 13.065 | 100.000 | 76.142 | 35.025 | 31.250 | 32.258 |
| Identical AA | 25 | 24 | 41 | 40 | 37 | 26 | 197 | 150 | 69 | 65 | 70 |
| Similar AA | 37 | 35 | 47 | 53 | 54 | 59 | 0 | 31 | 52 | 58 | 56 |
| MFDX2_ARATH | | | | | | | | | | | |
| % Identity | 13.568 | 9.645 | 15.920 | 17.588 | 20.000 | 17.413 | 76.142 | 100.000 | 36.364 | 30.653 | 34.653 |
| Identical AA | 27 | 19 | 32 | 64 | 40 | 35 | 150 | 197 | 72 | 61 | 70 |
| Similar AA | 37 | 40 | 65 | 35 | 59 | 51 | 31 | 0 | 51 | 65 | 63 |
| ADRX_YEAST | | | | | | | | | | | |
| % Identity | 15.517 | 16.000 | 18.994 | 16.949 | 19.022 | 19.886 | 35.025 | 36.364 | 100 | 29.798 | 33.333 |
| Identical AA | 27 | 28 | 34 | 30 | 35 | 35 | 69 | 72 | 172 | 59 | 61 |
| Similar AA | 31 | 28 | 49 | 50 | 44 | 50 | 52 | 51 | 0 | 52 | 56 |

TABLE 1B-continued

| Similarity of ferredoxins with eukaryotic sequences containing signal sequences | | | | | | | | | | | |
|---|---|---|---|---|---|---|---|---|---|---|---|
| | THEEB | SYNP2 | FER1_ARATH | FER2_ARATH* | FER3_ARATH | FER4_ARATH | MFDX1_ARATH | MFDX2_ARATH | ADRX_YEAST | ADX_HUMAN | FDX2_HUMAN |
| ADX_HUMAN | | | | | | | | | | | |
| % Identity | 10.811 | 11.170 | 16.23 | 17.617 | 18.135 | 15.426 | 31.25 | 30.653 | 29.798 | 100 | 30.688 |
| Identical AA | 20 | 21 | 31 | 34 | 35 | 29 | 65 | 61 | 59 | 184 | 58 |
| Similar AA | 37 | 37 | 55 | 44 | 57 | 57 | 58 | 65 | 52 | 0 | 61 |
| FDX2_HUMAN | | | | | | | | | | | |
| % Identity | 12.973 | 12.500 | 19.565 | 17.857 | 17.949 | 12.821 | 32.258 | 34.653 | 33.333 | 30.688 | 100 |
| Identical AA | 24 | 23 | 36 | 35 | 35 | 25 | 70 | 70 | 61 | 58 | 183 |
| Similar AA | 36 | 32 | 48 | 46 | 49 | 53 | 56 | 63 | 56 | 61 | 0 |

TABLE 1C

Similarity of ferredoxins with eukaryotic sequences with signal sequences removed
Without Signal Sequence

| | THEEB | SYNP2 | FER1_ARATH | FER2_ARATH* | FER3_ARATH | FER4_ARATH | MFDX1_ARATH | MFDX2_ARATH | ADRX_YEAST | ADX_HUMAN | FDX2_HUMAN |
|---|---|---|---|---|---|---|---|---|---|---|---|
| THEEB | | | | | | | | | | | |
| % Identity | 100 | 71429 | 59.184 | 59.184 | 59.434 | 48.485 | 15.244 | 21.600 | 23.077 | 16.000 | 18.045 |
| Identical AA | 98 | 70 | 58 | 58 | 63 | 48 | 25 | 27 | 27 | 20 | 24 |
| Similar AA | 0 | 16 | 25 | 26 | 25 | 31 | 37 | 37 | 31 | 37 | 35 |
| SYNP2 | | | | | | | | | | | |
| % Identity | 71.429 | 100.000 | 63.918 | 67.010 | 59.434 | 49.495 | 14.815 | 15.447 | 22.881 | 16.406 | 15.909 |
| Identical AA | 70 | 97 | 62 | 65 | 63 | 49 | 24 | 19 | 27 | 21 | 21 |
| Similar AA | 16 | 0 | 22 | 20 | 23 | 29 | 35 | 40 | 29 | 37 | 35 |
| FER1_ARATH | | | | | | | | | | | |
| % Identity | 59.184 | 63.918 | 100.000 | 86.458 | 58.491 | 53.535 | 16.049 | 15.873 | 20.175 | 16.800 | 18.321 |
| Identical AA | 58 | 62 | 93 | 83 | 62 | 53 | 26 | 20 | 23 | 21 | 24 |
| Simiar AA | 25 | 22 | 0 | 9 | 24 | 29 | 33 | 40 | 33 | 37 | 31 |
| FER2_ARATH* | | | | | | | | | | | |
| % Identity | 59.184 | 67.010 | 86.458 | 100.000 | 57.547 | 51.515 | 14.815 | 17.073 | 18.644 | 16.126 | 18.321 |
| Identical AA | 58 | 65 | 83 | 96 | 61 | 51 | 24 | 21 | 22 | 20 | 24 |
| Simlar AA | 26 | 20 | 9 | 0 | 26 | 31 | 39 | 45 | 31 | 34 | 31 |
| FER3_ARATH | | | | | | | | | | | |
| % Identity | 59.434 | 59.434 | 58.491 | 57.547 | 100.000 | 50.943 | 15.244 | 19.231 | 20.000 | 16.794 | 21.053 |
| Identical AA | 63 | 63 | 62 | 61 | 106 | 54 | 25 | 25 | 25 | 22 | 28 |
| Similar AA | 25 | 23 | 24 | 26 | 0 | 35 | 40 | 39 | 30 | 36 | 32 |
| FER4_ARATH | | | | | | | | | | | |
| % Identity | 48.485 | 49.495 | 53.535 | 51.515 | 50.943 | 100.000 | 11.728 | 19.512 | 17.797 | 15.152 | 13.740 |
| Identical AA | 48 | 49 | 53 | 51 | 54 | 99 | 19 | 24 | 21 | 20 | 18 |
| Similar AA | 31 | 29 | 29 | 31 | 35 | 0 | 40 | 36 | 33 | 41 | 37 |
| MFDX1_ARATH | | | | | | | | | | | |
| % Identity | 15.244 | 14.815 | 16.049 | 14.815 | 15.244 | 11.728 | 100.000 | 66.667 | 36.420 | 32.927 | 38.272 |
| Identical AA | 25 | 24 | 26 | 24 | 25 | 19 | 162 | 108 | 59 | 54 | 62 |
| Similar AA | 37 | 35 | 33 | 39 | 40 | 40 | 0 | 12 | 29 | 39 | 43 |
| MFDX2_ARATH | | | | | | | | | | | |
| % Identity | 21.603 | 15.447 | 15.873 | 17.073 | 19.231 | 19.412 | 66.667 | 100.000 | 47.967 | 43.200 | 45.455 |
| Identical AA | 27 | 19 | 20 | 21 | 25 | 24 | 108 | 123 | 59 | 54 | 60 |
| Similar AA | 37 | 40 | 40 | 45 | 39 | 36 | 12 | 0 | 30 | 38 | 38 |
| ADRX_YEAST | | | | | | | | | | | |
| % Identity | 23.077 | 22.881 | 20.175 | 18.644 | 20.000 | 17.797 | 36.420 | 47.967 | 100.000 | 38.710 | 36.641 |
| Identical AA | 27 | 27 | 23 | 22 | 25 | 21 | 59 | 59 | 112 | 48 | 48 |
| Similar AA | 31 | 29 | 33 | 31 | 30 | 33 | 29 | 30 | 0 | 35 | 39 |

TABLE 1C-continued

Similarity of ferredoxins with eukaryotic sequences with signal sequences removed
Without Signal Sequence

| | THEEB | SYNP2 | FER1_ARATH | FER2_ARATH* | FER3_ARATH | FER4_ARATH | MFDX1_ARATH | MFDX2_ARATH | ADRX_YEAST | ADX_HUMAN | FDX2_HUMAN |
|---|---|---|---|---|---|---|---|---|---|---|---|
| ADX_HUMAN | | | | | | | | | | | |
| % Identity | 16.000 | 16.406 | 16.800 | 16.126 | 16.794 | 15.152 | 32.927 | 43.200 | 38.710 | 100.000 | 31.579 |
| Identical AA | 20 | 21 | 21 | 20 | 22 | 20 | 54 | 54 | 48 | 124 | 42 |
| Similar AA | 37 | 37 | 37 | 34 | 36 | 41 | 39 | 38 | 35 | 0 | 46 |
| FDX2_HUMAN | | | | | | | | | | | |
| % Identity | 18.045 | 15.909 | 18.321 | 18.321 | 21.053 | 13.740 | 38.272 | 45.455 | 36.641 | 31.579 | 100.000 |
| Identical AA | 24 | 21 | 24 | 24 | 28 | 18 | 62 | 60 | 48 | 42 | 131 |
| Similar AA | 35 | 35 | 31 | 31 | 32 | 37 | 43 | 38 | 39 | 46 | 0 |

Delivery of the Fd-FNR System

Delivery of the Matching Fd-FNR system will depend on its application. For animal cells, viral vectors, linear DNA, circular DNA and artificial chromosomes can all be used to deliver Fd-FNR and the Fd-FNR dependent metabolic pathways into human cells or animal cells. This is not limiting, there are many standardized ways to deliver genes into cells that may also be used. In neuronal slice cultures and plants, ballistics may be used to deliver DNA encoding for the metabolic pathway along with the matching Fd-FNR system. DNA may be delivered in nanoparticles or by transfection. Transgenic animals, plants or microbes that contain the matching Fd-FNR systems may be produced using standard methods.

Applications for Matching Fd-FNR Systems of Different Species

The systems and methods disclosed herein have many uses, for example, in the following areas:

1) Gene therapy towards in vivo production of drugs;

2) Constructing transgenic animals, microbes or viruses that contain the systems disclosed herein;

3) Constructing viruses that infect cells and make them light sensitive, activating or repressing any gene of interest in a light dependent manner or for fluorescence imaging;

4) Constructing DNA parts containing the systems disclosed herein;

5) Research tools for genetic research, including pharmaceutical research, development, neurobiology, cognitive science, etc.;

6) Producing metabolites that require Fd-FNR systems for synthesis in a different species (for example, a mammalian or insect cell can produce a metabolite that is used as a drug that is naturally made by bacteria or plants); and 7) Producing synthetic organisms for bioremediation or detoxification, fixing nitrogen or photosynthesis.

Because Fds are the some of the most electronegative proteins in metabolic pathways, introducing the matching Fd for a different biosynthetic pathway could be key for efficiently producing a wide array of metabolites including lipids, sterols, dolichols, luciferins, quinones, carotenoids, nucleotides, nitrates/nitrogen, and sulfites. Some direct usages of the Fd-FNR for metabolite or in vivo drug production include, but are not limited to production of metabolites produced in different species, such as vitamins, hormones, carbohydrates etc. Table 2 outlines some specific Fd dependent metabolites in different classes. Because Fd is the most electronegative enzyme in the cell, it may also be indirectly necessary to increase production from different species for most metabolites. The disclosed concept can also be used to produce endogenous metabolites with enzymes from another species. This may allow for higher efficiency production, higher levels of production, or for regulating production.

TABLE 2

| Molecule/ Enzyme | Description | Related reaction | Reference |
|---|---|---|---|
| Calciol, Calcitriol | Vitamin-D3 analogs, pre-hormone and hormonally active metabolites, used to treat and prevent kidney and liver damage, low calcium levels, bone, kidney and parathyroid gland diseases. | Vitamin D3 + Oxygen + 2 Reduced ferredoxin + 2 $H^+$ <=> Calcidiol + 2 Oxidized ferredoxin + $H_2O$ or Calcidiol + Oxygen + 2 Reduced ferredoxin + 2 $H^+$ <=> Calcitriol + 2 Oxidized ferredoxin + $H_2O$ | Kegg Reaction: R11458 and R11459, respectively. Brandi, Maria Luisa, and Salvatore Minisola. "Calcidiol [25 (OH) D3]: from diagnostic marker to therapeutical agent." Current medical research and opinion 29.11 (2013): 1565-1572. |
| Violaxanthin | Pigment violaxathin reversibly converts to zeaxanthin in a ferredoxin-dependent and light-dependent manner, with photoprotective functions in plants. | Zeaxanthin + 4 Reduced ferredoxin + 4 $H^+$ + 2 Oxygen <=> Violaxanthin + 4 Oxidized ferredoxin + 2 $H_2O$ | Kegg Reaction: R10070. Jahns, Peter, Dariusz Latowski, and Kazimierz Strzalka. "Mechanism and regulation of the violaxanthin cycle: the role of antenna proteins and membrane lipids." Biochimica et Biophysica Acta (BBA)-Bioenergetics 1787.1 (2009): 3-14. |
| Thioredoxin | Small protein, plays a vital role in cellular redox homeostasis, implicated as having an important role in cancer. | 2 Reduced ferredoxin + Thioredoxin disulfide <=> 2 Oxidized ferredoxin + Thioredoxin + 2 $H^+$ | Kegg Reaction: R09502. Karlenius, Therese Christina, and Kathryn Fay Tonissen. "Thioredoxin and cancer: a role for thioredoxin in all states of tumor oxygenation." Cancers 2.2 (2010): 209-232. |

TABLE 2-continued

| Molecule/ Enzyme | Description | Related reaction | Reference |
|---|---|---|---|
| L-Glutamine | Alpha-amino acid, plays a role in many biochemical functions, including protein and lipid synthesis, cellular energy, muscle and normal brain functioning. | 2 L-Glutamate + 2 Oxidized ferredoxin <=> L-Glutamine + 2-Oxoglutarate + 2 Reduced ferredoxin + 2 $H^+$ | Kegg Reaction: R00021. Ziegler, Thomas R., et al. "Safety and metabolic effects of L-glutamine administration in humans." Journal of Parenteral and Enteral Nutrition 14.4_suppl (1990): 137S-146S. |
| Corticosterone | Steroid derived from cholesterol, involved in memory recognition and consolidation. | 11-Deoxycorticosterone + 2 Reduced ferredoxin + Oxygen + 2 $H^+$ <=> Corticosterone + 2 Oxidized ferredoxin + $H_2O$ | Kegg Reaction R03851. Smith, Eric M., Walter J. Meyer, and J. Edwin Blalock. "Virus-induced corticosterone in hypophysectomized mice: a possible lymphoid adrenal axis." Science 218.4579 (1982): 1311-1312. |
| Benzoyl-CoA | Coenzyme implied with different enzymes and used in studies of benzoate metabolism | 4-Hydroxybenzoyl-CoA + Reduced ferredoxin <=> Benzoyl-CoA + Oxidized ferredoxin + $H_2O$ | Kegg Reaction R05316. Harwood, Caroline S., et al. "Anaerobic metabolism of aromatic compounds via the benzoyl-CoA pathway." FEMS Microbiology reviews 22.5 (1998): 439-458. |
| Nitrogenase NifDK Tetramers | Nitrogenase NifDK Tetramers are fundamental for nitrogenase assembly, responsible for fixation of nitrogen. | $N^2$ + $8H^+$ + 8e−16 ATP + reduced MoFe protein (NifDK) + Reduced Ferredoxin + 8 reduced Ferredoxin oxireductase =>2 $NH_3$ + H2 + 16 ADP + oxidized MoFe protein (NifDK) + oxidized Ferredoxin + 8 oxidized Ferredoxin oxireductase | Kegg Reaction R05185. Burén, Stefan, et al. "Formation of Nitrogenase NifDK Tetramers in the Mitochondria of *Saccharomyces cerevisiae*." ACS Synthetic Biology (2017). |
| Phycocyanobilin (PCB) | Light sensing chromophore. | Biliverdin + 4 Reduced ferredoxin + Reduced PcyA <=> (3Z)-Phycocyanobilin + 4 Oxidized ferredoxin + Oxidized PcyA | Kegg Reaction R05817. |
| Phytochromobilin (PΦB) | Light sensing chromophore. | Biliverdin + 4 Reduced ferredoxin + Reduced Hy2 <=> (3Z)-Phytochromobilin + 4 Oxidized ferredoxin + Oxidized Hy2 | Kegg Reaction R05817. |
| Nucleotides | Ferredoxin reduces the Pyridine nucleotide and is involved in the formation of hydrogen | TPN + $H_2$ + Reduced Ferredoxin => TPNH + $H^+$ + Oxidized Ferredoxin | Valentine, R. C., Winston J. Brill, and R. S. Wolfe. "Role of ferredoxin in pyridine nucleotide reduction." Proceedings of the National Academy of Sciences 48.10 (1962): 1856-1860. |

This can be applied industrially to cost effective production of plant metabolites in microbes or for in vivo production of therapeutic metabolites by genetically encoding these metabolites' pathways from the species that naturally make them. More specifically, this concept may be applied to making bacterial, fungal or other microbial metabolites in plants or to making metabolites from one microbe in another, such as a bacterial metabolite in fungi. Some examples include: tetrapyrroles such as linear tetrapyrroles, phycocyanobilin, phytochromobilin, biliverdin, phycourobilin, phycoviolobilin, phycoerythrobilin, chlorophylls, porphyrins, corrinoids, other tetrapyrroles or other metabolites whose biosynthesis is Fd or FNR activity dependent. The system disclosed herein is not limited to producing phycobilins or chromophores. Other metabolites made in plants, bacteria or other different species that require additional Fd/FNR activity to reconstitute the metabolic pathway or to perform other cellular functions can be produced by the system and method disclosed herein. This technology may be used to produce transgenic animals, plants, yeast or bacteria.

This technology can be applied to make metabolites from a plant or microbe in humans, in other words a gene therapy drug delivery method or in vivo production of drugs.

Fd-FNR Matching Enables Genetically Encoded Red-Light Activated Gene Switch

Optical control of biology holds great promise as a tool for studying gene function, developmental biology, gene therapies and tissue engineering. The exquisite temporal and spatial precision achieved through optics has been used to develop an assortment of tools to control biological functions such as gene expression, neural activity, cell signaling, secretion, peroxisomal trafficking, and protein activity. However, most of these existing systems have significant limitations. Particularly, they are either not very robust, require sufficient presence of light-absorbing chromophores, interfere with the cells intracellular signaling pathways, or the wavelength of light used penetrates tissue poorly. The near-infrared (NIR) spectrum is the ideal window for optical control of biology in mammalian cells. This patent document discloses biosynthetic enzymes transferred from the metabolism of different species to genetically encode the production of two NIR-responsive chromophores. In addition, it is shown that increasing the production of phycocyanobilin (PCB) in mammalian cells enables the development of a robust genetically encoded Red-light Activated Gene Switch (RAGS), that is compatible with other phytochrome B (PhyB) based optogenetic systems.

Figure 1:
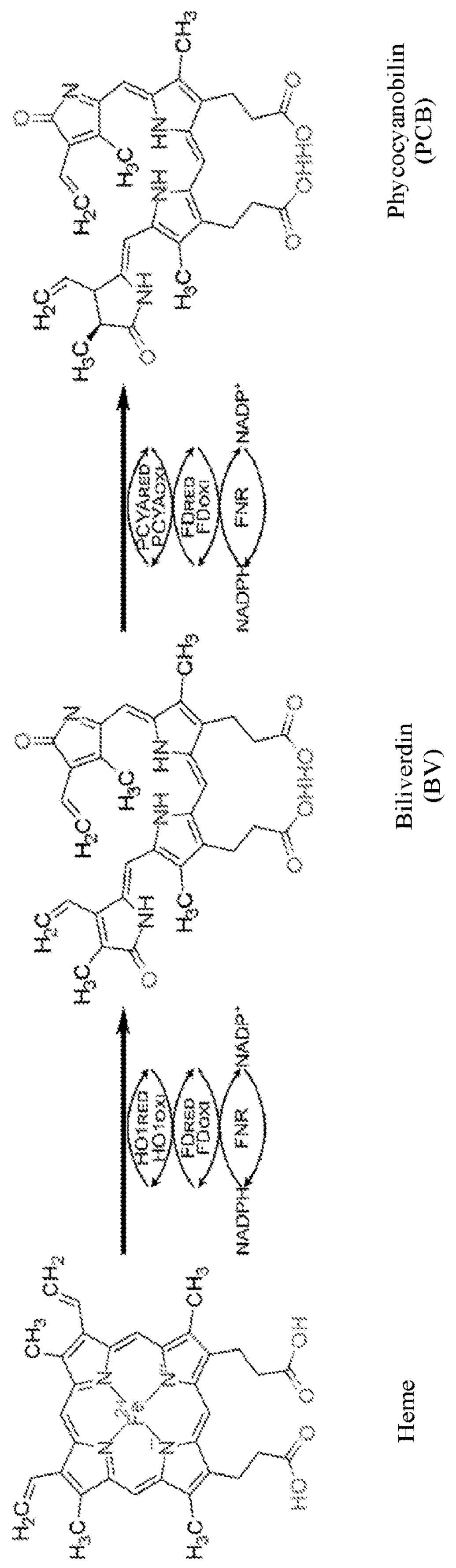
FIG. 1 shows the metabolic pathway for PCB biosynthesis pathway including the NADPH/FNR/Fd redox cascade (i.e. the Fd-FNR system or the Fd-FNR reduction system). In the first reaction reduced HO1 ($HO1_{RED}$) binds heme and reduces it into biliverdin (BV), converting $HO1_{RED}$ into oxidized HO1 ($HO1_{OX1}$). Next, reduced ferredoxin ($Fd_{RED}$) binds to and reduces $HO1_{OX1}$, back into $HO1_{RED}$, converting $Fd_{RED}$ into oxidized Fd ($Fd_{OX1}$). Next, $Fd_{OX1}$ binds to FNR bound to NADPH. NADPH reduces $FD_{OX1}$ back into $Fd_{RED}$, forming $NADP^+$. FNR bound $NADP^+$ is replaced by NADPH, completing the cycle (NADPH is regenerated from $NADP^+$ by the cell in a separate pathway/cycle). A similar cycle occurs in the second reaction to produce PCB from BV. BV from the first reaction binds to reduced PcyA ($PcyA_{RED}$), reducing BV into phycocyanobilin (PCB) and converting $PcyA_{RED}$ into oxidized PcyA ($PcyA_{OX1}$). Next, reduced ferredoxin ($Fd_{RED}$) binds to and reduces $PcyA_{OX1}$ back into $PcyA_{RED}$, while $Fd_{RED}$ becomes oxidized ($Fd_{OX1}$). Next, $Fd_{OX1}$ binds to FNR bound to NADPH, NADPH reduces $Fd_{OX1}$ back into $Fd_{RED}$ and forming $NADP^+$. FNR bound $NADP^+$ is replaced by NADPH, completing the cycle (NADPH is regenerated from $NADP^+$ by the cell in a separate pathway/cycle). Many other enzymes also use the same mechanism, in that they are reduced by Fd, which is then reduced by NADPH bound to FNR. Examples of other Fd-FNR dependent enzymes/metabolites are listed in Table 2. They represent several classes of metabolites/enzymes, therefore this Fd-FNR matching concept/technology is not limited to those specific metabolites.

NIR-responsive chromophores like PCB and phytochromobilin (PΦB) are used by phytochrome systems in cyanobacteria, algae, and plants, but are not naturally made in some bacteria, animal cells, or many fungal species. These metabolites are produced by the enzymes phycocyanobilin: ferredoxin oxidoreductase (PcyA) and phytochromobilin: ferredoxin oxidoreductase (Hy2), respectively, from Biliverdin IXα (BV), a degradation product of heme. The metabolic pathway for PCB synthesis is illustrated in FIG. 1. Several prior publications have shown that it is possible to produce these chromophores in *E. coli* by expressing PcyA or Hy2 without adding the matching ferredoxin (Fd) and ferredoxin-NADP$^+$-reductase (FNR) reduction system. Likewise, it was reported that PCB production was tested in mammalian cells by expressing PcyA and HO1, but there was no direct measurement of chromophore production. It was reasoned that mitochondrial placement of PcyA and HO1 in the same cellular compartment where the chromophore precursor (heme) is produced would enhance PCB production. However, because mammalian cells also express Fd and FNR (Fd+FNR) exclusively in the mitochondria, those prior experiments did not address the possibility that PCB production failed to occur in the cytoplasm because of the mitochondrial localization of Fd+FNR.

Also disclosed are methods of optimizing Red-light Activated Gene Switch (RAGS) by customizing the levels of activation or promoter leakiness (promoters that drive mRNA production at a lower level even when not activated) to tailor it for specific applications. As demonstrated in the working examples, modifying the promoter can greatly affect the level of activation at the expense of leakiness. It was found that the MTAD activation domain is an equally strong activator to VPR (FIG. 11C), however, VPR is 8.9× larger in molecular weight than MTAD. There are still other permutations of gene fusions that were not tested in the study that may further enhance RAGS, such as DBD on the N-terminus of PhyB or optimizing linker sequences. It may also be the case that using a stronger or tissue-specific promoter to drive expression of PCB or PΦB biosynthetic enzymes could lead to higher activation levels or restrict light sensitivity to specific cell types. Some examples are the synapsin promoter that restrict expression to neurons, the parvalbumin promoter that restricts expression to interneurons, desmin that restricts it to muscle tissue, ICAM promoter that restricts expression to endothelial cells, or INFβ that restricts expression to hematopoietic cells etc. Similarly, there are many additional promoters in non-mammalian species, such as Gal4 in yeast, Aspartyl protease promoter that restricts expression to cortex in *Arabidopsis*, or engrailed in *Drosophila* that can be utilized to restrict expression to certain cell types or stages of development.

As demonstrated in the working examples, the genetically encoded system disclosed herein works robustly in several cell types and can be used widely in optogenetics. For example, with RAGS, it is possible to make light-sensitive model organisms to instantaneously control genes deep into tissue. The endogenous production of chromophores like PCB enables the in vivo use of several existing and compatible optogentic tools to regulate cell signalling, cell migration, or protein localization. RAGS, a fully endogenous NIR-PhyB switch with Fd+FNR matching, provides long sought goals for non-invasive optogenetics and genetically-efficient encoded production of a multitude of metabolites from one species in another. Some usages of this optogenetic system are for controlling genes in animal models or for gene therapies. For example, it can be used to control the insulin gene or other peptide hormone on and off, peptides that target cancer, or expressing recombinant antibodies in a regulated manner.

Phytochromes are promising candidates for improving light delivery for imaging and optical control of biology. Used by plants, cyanobacteria, and some fungi for sensing of environmental light stimuli, many phytochromes evolved to require minimal light for activation and to absorb light in the NIR window. These are inherent properties of many proteins with a bilin chromophore, like phytochromes, because: i) the chromophores are very sensitive to light (high absorbance/extinction coefficient) and ii) the chromophores bound to the phytochrome can have a long-lived activation state, ranging from tens of minutes to hours. As tools for controlling biology with light, PhyB has these optical characteristics and has been shown to be very robust compared to other switches, but required external addition of a chromophore, limiting them to in vitro applications. Genetically encoding mammalian cells to produce these chromophores allows the development of a robust NIR gene switch that is fully genetically encoded, removing these barriers for in vivo applications.

RAGS is the most light sensitive optogenetic system to date: the peak intensity required for maximal activation is at most 2 nWatts/mm$^2$. For comparison, it requires 500,000×-2,500,000× less light than the peak activation for stimulating neurons with ChR2 and is 50-100× more sensitive than other phytochrome-based gene switches in yeast and mammalian cells. By combining the ability of red light to penetrate deeply into tissue with the low light requirements for maximal activation of RAGS, it is possible to use light to control genes deeper into tissues than ever before. RAGS has great potential in animal studies and light-modulated gene therapies. More broadly, Fd+FNR matching has a potential to enable new areas of synthetic biology.

The following working examples are included for the sole purpose of illustration. By no means, the working examples described below limit the scope of this disclosure.

Example 1 Methods

Zinc-PAGE-Immunoprecipitation assays. Protein G PLUS-Agarose beads were prepared by adding 200 μg anti-HA (clone HA-7, Sigma H9658) into 2 ml 25% agarose. After overnight binding at 4° C., unbound anti-HA was washed off with four PBS washes. For each 6-well plate, 500×$10^3$ HEK293 cells were transfected using 2.5 μg DNA in total and 6 μl of Lipofectamine™ 2000 per well (ThermoFisher Scientific). For heme experiments, media or media containing 1 μM heme (Frontier Scientific H651-9) dissolved at 10 mM in 100 mM NaOH and sterile filtered with a 0.22 μM filter (Millipore SLGP033RS), was changed 18 hours after transfection and again 43 hours after transfection. Cells were then harvested with RIPA buffer (1% Triton™ X-100, 0.5% Sodium Deoxycholate, 25 mM Tris pH8.0, 150 mM NaCl, 0.10% SDS and 2.5 mM EDTA, 2× protease inhibitors (Sigma, P8340-1ML), sonicated briefly and centrifuged for 30 minutes at 21,000 g. BCA assays (ThermoFisher Scientific, 23225) were used to determine protein concentration of resulting supernatant/lysates. Equal masses of each protein sample were diluted with two parts of PBS, then loaded onto Protein G PLUS-Agarose beads. Next beads were washed, and boiled in sample buffer (30% glycerol, 10% SDS, 300 mM Tris pH 6.8, 0.03% Bromophenol Blue, 179 mM 2-Mercaptoethanol). After PAGE, gels were incubated in running buffer containing 10 mM Zinc Acetate for 10 minutes prior to imaging in a FluorChem™ E (Protein Simple). Gels were then transferred onto nitrocellulose and probed with primary antibody anti-HA 1:5000 (Sigma, clone HA-7, H9658), and by Goat anti-Mouse secondary antibody 1:5000 (ThermoFisher, 32230). Western blots were imaged in a FluorChem™ E (Protein Simple). Gel bands were quantified using the FIJI (ImageJ) gel analysis tool, as described by Schindelin et al., Nat. Methods 9: 676-682 (2012).

Imaging PCB production. HEK293 cells (100×$10^3$) were transfected 24 hours after plating on polylysine (Sigma P6407-5 mg) coated coverslips. 43 hours later media was changed with fresh media or media+10 uM PCB (FIG. 6) or media+5 μM PCB (FIG. 7) (Frontier Scientific P14137) for the NE+PCB control. One hour later cells were rinsed in PBS and fixed in 4% Paraformaldehyde for 10 minutes. Next cells were washed with PBS before incubating in permeabilization buffer (5% BSA+0.3% Triton™ X-100 in PBS) for 30 minutes, followed by primary antibodies overnight at 4° C. in antibody buffer (2% BSA+0.2% Triton™ X-100 in PBS; anti-FLAG mouse monoclonal 1:1000 (Sigma F3165) anti-HA rabbit polyclonal 1:500 (Santa Cruz Y-11). Coverslips were washed in PBS followed by primary antibodies overnight at 4° C. in antibody buffer (2% BSA+0.2% Triton™ X-100 in PBS). Next coverslips were washed in PBS and incubated in antibody buffer with goat anti-mouse Alexa Fluor® 488 1:1000 (ThermoFisher A11001), goat anti-rabbit Alexa Fluor® 568 1:1000 (ThermoFisher A11011). Coverslips were then mounted with Fluoromount-G® (SouthernBiotech 0100-20). Images were taken using a DeltaVision® RT Deconvolution Microscope and processed using FIJI/ImageJ.

Cell culture, transfection, light induction and reporter gene assays. Human Embryonic Kidney 293 cells (HEK293, ATCC CRL-1573) were cultivated in Dulbecco's Modified Eagle Medium (DMEM, Gibco) supplemented with 10% fetal bovine serum (FBS, Gibco) and 100 U/ml of penicillin and 0.1 mg/ml of streptomycin (Gibco). All cells were cultured under 5% $CO_2$ at 37° C. Cells were seeded at 100,000-125,000 HEK293 cells per well in 24-well plates, 24 hours before transfection. Transient transfection of plasmids was achieved through lipofection following the manufacturer's instructions and protocol (Lipofectamine™ 2000, ThermoFisher, 11668019). For each transfection reaction, a total of 0.5 μg plasmid DNA, was combined at specific molar ratios for each experiment as detailed in Table 3. Genes for enzymes were synthesized by Genscript and Integrated DNA Technologies.

TABLE 3

Plasmids Used

| Plasmid Numbe | Description |
|---|---|
| pPKm-118 | pcDNA3 - pCMV - 5X UAS - pFR Luciferase |
| pMZ-802 | FLuc under control of a modified PTet (tetO13-PhCMVmin- FLuc-pA) |
| pM3-VP16 | Positive Control Vector, expresses a fusion of the GAL4 DNA-BD to the VP16 AD |
| pPKm-102 | pcDNA3 - pCMV - mOrange, plasmid expressing orange fluorescent protein (OFP) |
| pPKm-105 | pcDNA3 - pCMV - PhyB NT - GBD, expressing Phytochrome B (PhyB) with Gal Binding Domain (GBD), under CMV promoter |
| pPKm-112 | pcDNA3 - pCMV - MTAD - PIF3, expressing Phytochrome interacting factor 3 (PIF3) and minimal transactivation domain (MTAD), under CMV promoter |
| pPKm-113 | pcDNA3 -pCMV - MTAD - PIF6, expressing the Phytochrome interacting factor 6 (PIF6) and MTAD, under CMV promoter |
| pPKm-121 | Control reporter for constitutive expression of wildtype Renilla luciferase (Rluc) under pRL-TK |
| pPKm-145 | Empty plasmid, pSIN-EF1-alpha-IRES-puro |
| pPKm-163 | pcDNA3 - pCMV - PIF3 - DBD, expressing PIF3 and DBD, under CMV promoter |
| pPKm-195 | pcDNA3 - pCMV - PhyB - MTAD, expressing PhyB and MTAD, under CMV promoter |
| pPKm-196 | pcDNA3 - pCMV - PIF6 - DBD, expressing PIF6-DBD under CMV promoter |
| pPKm-202 | pcDNA3 - pCMV - 5X UAS - pFR - CMVmin Luciferase |
| pPKm-226 | pcDNA3 - pCMV - PIF3 - VPR, expressing PIF3 and VPR transactivator domain, under CMV promoter |
| pPKm-227 | pcDNA3 - pCMV - VPR - PIF3, expressing VPR transactivator domain and PIF3, under CMV promoter |
| pPKm-230 | pSIN - EF-1alpha - PIF3 - MTAD - IRES - PhyB - GBD, dual vector of PIF3-MTAD under EF-1 alpha promoter and PhyB- DBD under IRES promoter |

TABLE 3-continued

| Plasmids Used | |
|---|---|
| Plasmid Numbe | Description |
| pPKm-231 | pSIN - EF-1alpha - MTS - tFd - P2A - MTS - tFNR, vector encoding for mitochondrial-tagged *Thermosynechococcus* elongates Ferredoxin (Fd) and Ferredoxin-NADP(+) oxireductase (FNR), under EF-1alpha promoter |
| pPKm-232 | pSIN - EF-1alpha - MTS tHO1 - P2A - MTS - tPCYA, vector encoding for mitochondrial-tagged *Thermosynechococcus* elongates Heme Oxigenase-1 (HO1) and Phycocyanobilin:ferredoxin oxireductase, under EF-1alpha promoter |
| pPKm-233 | pSIN - EF-1alpha - sFd - P2A - MTS - sFNR, vector encoding for *Synechococcus* sp. Ferredoxin (Fd) and Ferredoxin-oxireductase (FNR) |
| pPKm-234 | pSIN - EF-1alpha - MTS sHO1 - P2A - MTS - sPCYA, vector encoding for mitochondrial-tagged *Synechococcus* sp. Heme Oxigenase-1 (HO1) and Phycocyanobilin:ferredoxin oxireductase (PcyA), under EF-1alpha promoter |
| pPKm-235 | pSIN - EF-1alpha - MTS sHO1 - P2A - MTS - sPCYA, vector encoding for mitochondrial-tagged *Synechococcus* sp. Heme Oxigenase-1 (HO1) and phytochromobilin:ferredoxin oxidoreductase (Hy2) |
| pPKm-240 | pSIN - EF-1alpha - Cyto - sFd - P2A - Cyto - sFNR, vector encoding for cytoplasmic-tagged *Synechococcus* sp. Heme Oxigenase-1 (HO1) and Phycocyanobilin:ferredoxin oxireductase (PcyA), under EF-1alpha promoter |
| pPKm-243 | mOrange and mitochondrial-tagged sfGFP (pSIN-OFP-mitosfGFP) |
| pPKm-244 | pSIN - EF-1alpha - MTS - tHO1 - P2A - MTS - tPCYA - IRES - MTS - tFd - P2A - MTS - tFNR |
| pPKm-245 | pSIN - EF-1alpha - MTS - tHO1 - P2A - MTS - tPCYA - P2A - MTS - tFd - P2A - MTS - tFNR |
| pPKm-248 | pSIN - EF-1alpha - MTS - tPCYA - IRES - MTS - tHO1 - P2A - MTS - tFd - P2A - MTS - tFNR |

A construct with *Renilla* Luciferase reporter plasmid DNA was included as a control in all transfections. The culture medium was replaced with fresh medium 24 hours after transfection and the plates were placed inside black boxes (Hammond Manufacturing Company, 1591ESBK) for the remainder of the experimental procedure. For conditions where external PCB is added, 15 μM of PCB (Frontier Scientific P14137) in DMSO (Santa Crz Biotechnology, sc-202581) was supplemented in fresh medium 24 h after transfection.

Light induction was programmed to start 12 hours after medium replacement. Each black box was equipped with a circuit consisting of six red LEDs (660 nm, Thorlabs), except for the dark and far-red boxes which had no LEDs or a single far-red LED (73 nm, Thorlabs), respectively. In addition, each black box circuit was designed to allow for fine adjustment of light intensity (circuitry shown in FIG. 2), from 0.05 to 200 $\mu mol/m^2/s$. Light intensity was measured in μW at the cell level, converted to $\mu mol/m^2/s$ (light sensor area=63.6 $mm^2$), and adjusted for each experiment design using Sper Scientific Direct's Laser Power Meter (SSD, 8400). Detailed information on wavelengths, illumination intensity and duration used for each experimental procedure and data shown are detailed in each example below. Pulse duration and total illumination times were electronically controlled via a LabVIEW™ computer driving an Arduino® microprocessor, detailed below. Twelve hours after the 24 hours illumination cycle ended, cells were harvested for luciferase assays.

Figure 2:
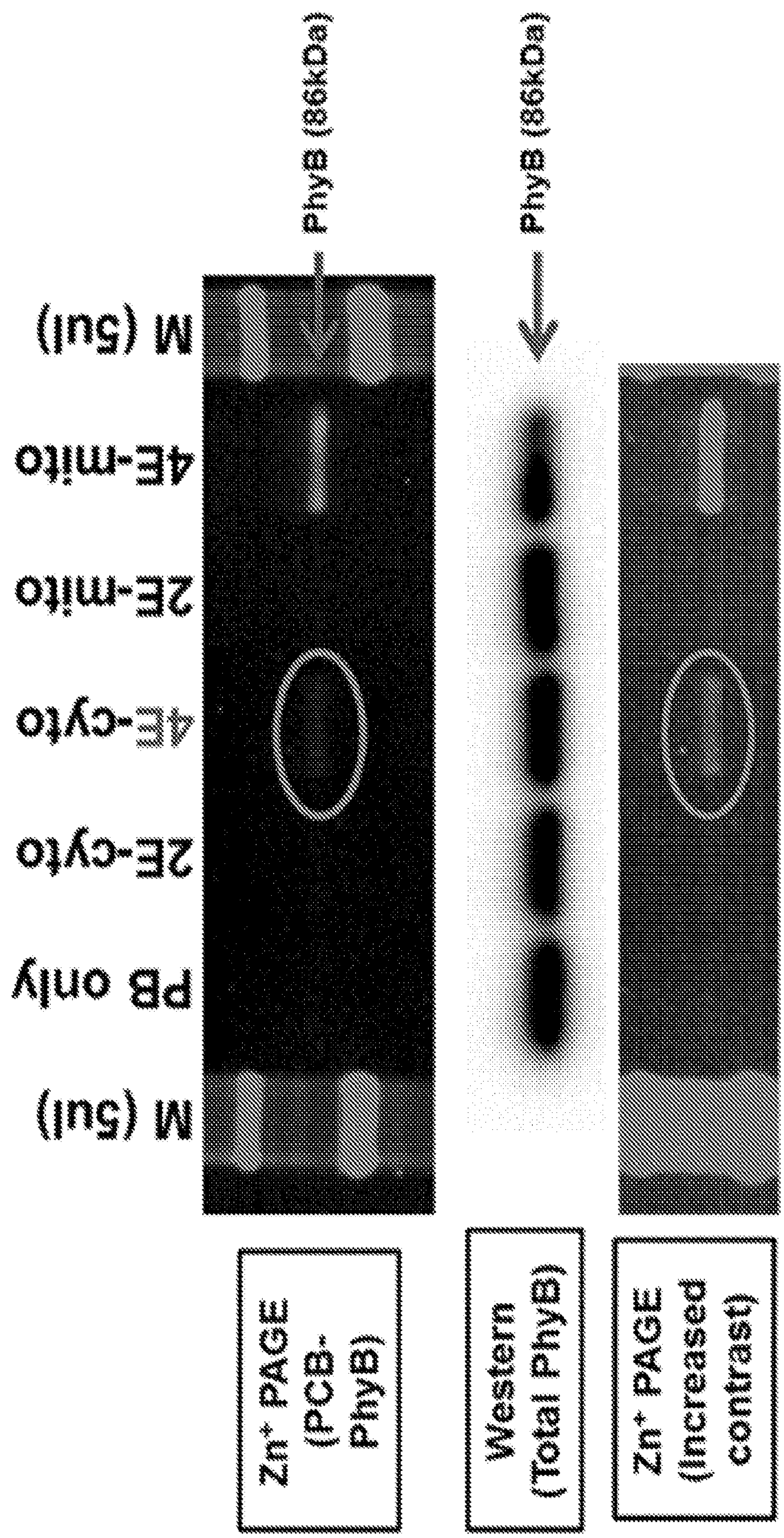
FIG. 2 shows that production of the metabolite PCB in mammalian cells requires the Fd+FNR system ("4E-cyto" and "4E-mito" refers to the system's enzymes with sublocalization in the cytoplasm and mitochondria, respectively). 2E refers to only two enzymes required for the metabolite's production are present (namely HO1 and PcyA), whereas 4E refers to the presence of HO1 and PcyA, as well as the Fd+FNR system's enzymes. As shown by Zn-PAGE, the bacterial Fd+FNR system (4E-cyto and 4E-mito) is required for PCB synthesis in both the cytoplasm and the mitochondria.

The light control system uses an Arduino® Uno and control circuitry, managed through a user interface developed in LabVIEW™ (National Instruments). A schematic of the system is shown in FIG. 2. Using this system, precise timing and light-intensity control were achieved for 8 experimental boxes that required red and/or far-red illumination. Each box can house a standard 6-well, 12-well, 24-well, 96-well plate or can be fitted for single dishes with minimum modifications. The system can be replicated for experiments requiring a larger number of boxes or experimental conditions. Far-red and red lights can be controlled independently if placed within the same box. For the experimental setup, boxes contained either far-red LEDs or red LEDs.

To obtain the reliable, consistent and robust control needed to drive the high-power LEDs used in the light control system, the circuit shown in FIG. 3 was designed. Coupled with the Arduino® signals, this system was able to deliver precise timing and intensity control to the illumination boxes. The circuit delivers a constant current using a LM317T linear voltage regulator (STMicroelectronics), a NPN general-purpose amplifier (2N2222, Fairchild Semiconductors), a resistor and a trimmer potentiometer (Helitrim, model 75PK10K). An external power supply was outfitted for the circuit (Safety Mark, 12V 1.5 A Switch-mode power supply). The power supply allows the circuit to vary its current and voltage needs depending upon the intensity chosen by user using the trimmer potentiometer.

The LabVIEW™ user interface, available for download at github.com/mcatanho/SupplementalMaterials_RAGS, controls the Arduino® and connected circuits. It allows the user to connect to the Arduino® effortlessly and to control experimental conditions such as time delay before illumination, total duration of sample illumination, and pulse frequencies for each individual illumination box. It also contains digital displays of all relevant experimental times (FIG. 2).

Luciferase Activity Assay. Luciferase assays were carried out using the Dual-Luciferase® Assay system (Promega), and following the manufacturer's protocol. Firefly and *Renilla* Luciferase activities were measured from cell lysates using the luminometer module of the Infinite® 200 PRO multimode reader (Tecan). Results of luciferase activity assays are expressed as a ratio of firefly luciferase (Fluc) activity to *Renilla* luciferase (Rluc) activity.

Illumination Circuits and Software. The light control system employs an Arduino® Uno and a light intensity control circuit (FIG. 3) driven by a user interface developed in LabVIEW™ (National Instruments) to control each box's LED intensity (FIG. 2). This system is ideal for precise timing and light-intensity control of each experimental box, while allowing for user-determined experimental start delay, illumination frequencies, and control of total duration of the experiment.

Kinetic Model. Using PySB, an in silico model is established to describe the biochemical interactions among the enzymes that compose the hypothesized PCB-production pathway, as shown in FIG. 1. PySB is a framework to create mathematical models of biochemical systems, relying on standard scientific Python libraries such as Numpy and Scipy, described by Lopez et al., Mol. Syst. Biol. 9: 646 (2013). It allows for the creation of biochemical pathways using a rule-based model with underlying coupled, first order, ordinary differential equations (ODEs), which makes this approach reusable, accurate and transparent. The PySB code, model equations and simulation files are available for download at github.com/mcatanho/SupplementalMaterials_RAGS. The quantitative mathematical model was parametrized (Table 4) by experimental data and uses simple ordinary differential equations to describe the changes in concentration of the molecular components of the reaction.

TABLE 4

Parameters for the model

| Parameter | Value | Description |
|---|---|---|
| k1 | 3.64556962e−01 c/s | $HO1_{red}$ and heme binding rate, towards Bv production |
| k2 | 1e−8 c/s | $HO1_{red}$ and heme unbinding rate |
| k3 | 1.14210526e+01 c/s | Bv production rate, oxidation of HO1 |
| k4 | 2.70526316e+01 c/s | $HO1_{oxi}$ and Fd:FNR binding rate, redox of HO1 |
| k5 | 1e−8 c/s | $HO1_{oxi}$ and Fd:FNR unbinding rate |
| k6 | 2.70526316e+01 c/s | Final $HO1_{red}$ reduction rate |
| k7 | 1.38947368e+01 c/s | Rate of reduction of Fd:FNR |
| k8 | 6.70126582e+01 c/s | $PcyA_{red}$ and Bv binding rate, towards PCB production |
| k9 | 1e−8 c/s | $PcyA_{red}$ and Bv unbinding rate |
| k10 | 5.26315789e+01 c/s | PCB production rate, oxidation of PcyA |
| k11 | 4.78947368e+01 c/s | $PcyA_{oxi}$ and Fd:FNR binding rate, redox of PcyA |
| k12 | 1e−8 c/s | $PcyA_{oxi}$ and Fd:FNR unbinding rate |
| K13 | 9.87354430e+01 c/s | Final $PcyA_{red}$ reduction rate |
| $k_{deg}$, BV | 1.084e−2 c/s | Degradation of Biliverdin |
| $k_{deg}$, PCB | 2.54e−2 c/s | Degradation of PCB |
| Heme, at t = 0 | 10 c | Initial concentration of Heme |
| HO-1, at t = 0 | 0.1 c | Initial concentration of HO-1 (red and oxi) |
| PcyA, at t = 0 | 0.1 c | Initial concentration of PcyA (red and oxi) |
| Fd:FNR, at t = 0 | 0.02 c | Initial concentration of Fd:FNR (red and oxi) |

c: arbitrary unit of concentration

Unless indicated otherwise, all other concentrations were considered to be zero.

The following ordinary differential equations governing the behavior of the model:

Scheme 1

$$\frac{d[Heme](t)}{dt} = -k_1[Heme][HO1_{red}] + k_2[HO1_{red}:Heme] \quad (1)$$

$$\frac{d[HO1_{red}](t)}{dt} = -k_{1r}[Heme][HO1_{red}] + k_2[HO1_{red}:Heme] + k_6 * [Fd:FNR_{red}:HO1_{oxi}] \quad (2)$$

$$\frac{d[Fd:FNR_{red}](t)}{dt} = k_7[Fd:FNR_{oxi}] - k_{11}[PcyA_{oxi}][Fd:FNR_{red}] + k_{12}[Fd:FNR_{red}:PcyA_{oxi}] - k_4[Fd:FNR_{red}][HO1_{oxi}] + k_5[Fd:FNR_{red}:HO1_{oxi}] \quad (3)$$

$$\frac{d[HO1_{red}:Heme](t)}{dt} = k_1[HO1_{red}][Heme] - [\![ (k ]\!]_2 + k_3)[HO1_{red}:Heme] \quad (4)$$

$$\frac{d[Bv](t)}{dt} = -k_8[Pcya_{red}][Bv] + k_3[HO1_{red}:Heme] - k_{14}[Bv] + k_9[Bv:PcyA_{red}] \quad (5)$$

$$\frac{d[HO1_{oxi}](t)}{dt} = -k_4[Fd:FNR_{red}][HO1_{oxi}] + k3[HO1_{red}:Heme] + k_5[Fd:FNR_{red}:PcyA_{red}] \quad (6)$$

$$\frac{d[Fd:FNR_{red}:HO1_{oxi}](t)}{dt} = k_4[Fd:FNR_{red}][HO1_{oxi}] - (k_5 + k_6)[Fd:FNR_{red}:HO1_{oxi}] \quad (7)$$

$$\frac{d[Bv:Pcya_{red}](t)}{dt} = k_8[PcyA_{red}][Bv] - (k_9 + k_{10})[Bv:PcyA_{red}] \quad (8)$$

-continued $$\frac{d[Fd{:}FNR_{oxi}](t)}{dt} = -k_7[Fd{:}FNR_{oxi}] + k_{13}[Fd{:}FNR_{red}{:}PcyA_{oxi}] + k_6[Fd{:}FNR_{red}{:}HO1_{oxi}] \quad (9)$$

$$\frac{d[PCB](t)}{dt} = -k_{15}[PCB] + k_{10}[Bv{:}PcyA_{red}] \quad (10)$$

$$\frac{d[PcyA_{oxi}](t)}{dt} = -k_{11}[PcyA_{oxi}][HO1_{red}] + k_{12}[Fd{:}FNR_{red}{:}PcyA_{oxi}] + k_{10}[Bv{:}PcyA_{red}] \quad (11)$$

$$\frac{d[Fd{:}FNR_{red}{:}PcyA_{oxi}](t)}{dt} = k_{11}[Fd{:}FNR_{red}][PcyA_{oxi}] - (k_{12} + k_{13})[Fd{:}FNR_{red}{:}PcyA_{oxi}] \quad (12)$$

In a more concise way, production of PCB can be described by the set of sequential steps shown in Table 5, and depicted in FIG. 1.

TABLE 5

Reactions modeled for the PCB production pathway

| Step | Reaction | Rate Constan | Description |
|---|---|---|---|
| 1 | Heme + $HO1_{red}$ → $HO1_{oxi}$ + BV | $k_1$, $k_2$, $k_3$ | Heme is reduced by $HO1_{red}$ to produce Biliverdin IX-α (BV) |
| 2 | $HO1_{oxi}$ + Fd:$FNR_{red}$ → $HO1_{red}$ + Fd:$FNR_{oxi}$ | $k_4$, $k_5$, $k_6$ | HO1 is brought back to its reduced state through the Fd:FNR oxidative pathway |
| 3 | BV + $PcyA_{red}$ → $PcyA_{oxi}$ + PCB | $k_8$, $k_9$, $k_{10}$ | BV is reduced by $PcyA_{red}$ to produce PCB |
| 4 | $PcyA_{oxi}$ + Fd:$FNR_{red}$ → $PcyA_{red}$ + Fd:$FNR_{oxi}$ | $k_{11}$, $k_{12}$, $k_{13}$ | PcyA is brought back to its reduced state through the Fd:FNR |
| 5 | Fd:$FNR_{oxi}$ → Fd:$FNR_{red}$ | $k_7$ | Redox of Fd:FNR |
| 6 | PCB → 0 | $k_{deg,PCB}$ | Degradation of PCB |
| 7 | BV → 0 | $k_{deg,BV}$ | Degradation of BV |

Figure 4:
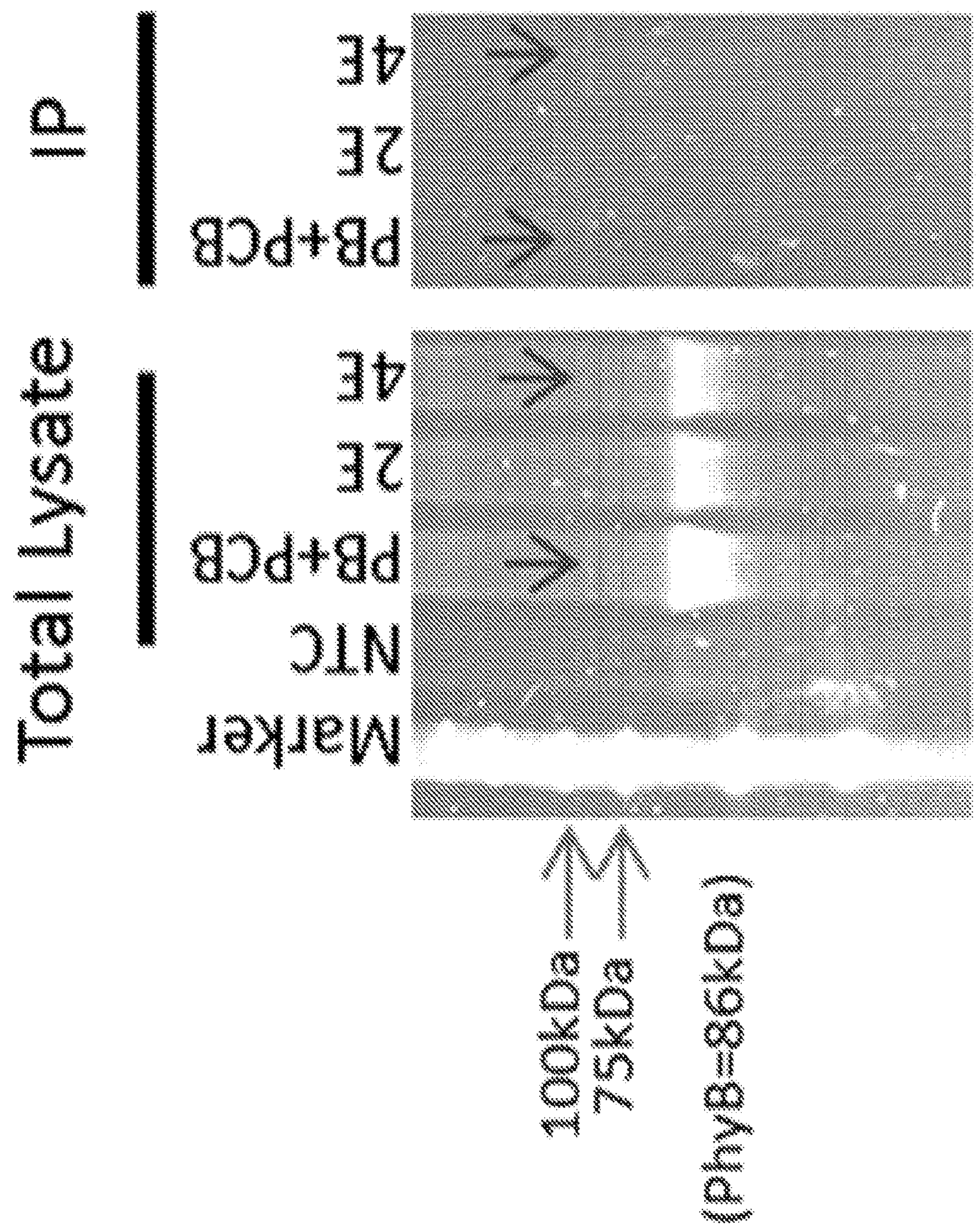
FIG. 4 shows the Fd+FNR dependence of PCB production by PcyA+HO1 in mammalian cells. PCB production requires both HO1-PcyA (2E) and Fd-FNR (4E).

Degradation of heme was not considered since it was assumed there were saturating amounts in the cell medium. Production of PCB is described in equation (10), and parameter $k_{10}$ represents the rate at which the chromophore is produced in a cell. The model assumes that those metabolites are present in vitro at stoichiometry levels compatible with the transient transfection. HO1 catalyzes the electron reduction of heme to BV, in the presence of Fd and FNR. PcyA, in turn, catalyzes the four electron reduction of BV to PCB. The Fd and FNR complex is of paramount importance to the redox metabolism in plants and cyanobacteria, working as an electron transfer complex to reduce or oxidize enzymes in different pathways, further acting to reduce or NADP+ to NADPH or the reverse of this reaction. As the preferred electron donor for HO1 and PcyA, the Fd+FNR complex reduces HO1 and PcyA, allowing for continuous turnover of those enzymes in the PCB production pathway. Studies have shown that Fd+FNR form binary complexes with FNR:NADP+, catalyzing electron transfer from reduced Fd to NADP+ at high rates producing NADPH. NADP+ and NADPH serve as the redox cofactor in those reactions. The recycling of Fd+FNR in the NADPH oxidative pathway was captured by the model described herein, parametrized by constant $k_7$. Since the plasmids used are transiently transfected, replication is not assumed. The proposed model was probed directly as proposed in literature, and similar pathways published previously. The model's agreement with the hypothesized pathway is shown in this disclosure, confirming that in the presence of heme, Fd and FNR are the rate limiting factors for the production of PCB, as seen in FIG. 4A, 4C, 4D and confirmed experimentally in FIG. 4E.

Example 2 Kinetic Model Development and Parametrization

Using PySB and coupled, first order, ordinary differential equations (ODEs), parametrization of the model was performed assuming that the reporter protein concentration follows the dynamics corresponding to PCB's concentration in the cells, such that PCB levels can be assumed to be linearly correlated to the protein's concentration at any specific time. As such, protein levels determined experimentally by fluorescence measurements were used to parametrize the model in Equations (1-12) as reported in the following section, in combination with literature findings, through a parameter sweep fit (based on data shown in FIG. 4E, Table 3).

Derivation of the Rule-Based Model

The rule-based model simulates PCB production as described by the activity states of HO1 and PcyA, in the following scheme (Scheme 1): In the first redox reaction of the PCB pathway, (1) heme oxignenase (HO1) catalyzes the rate-limiting step in the degradation of Heme, to yield equimolar amounts of Iron (Fe), carbon monoxide (CO), and Bbiliverdin IXα (Bv). In the following oxidative reaction, (2) Biliverdin is metabolized to Phycocyanobilin by PcyA. PcyA and HO1 are reduced through the ferredoxin (Fd) and ferredoxin-NADP+-reductase (FNR) oxidative pathway (FIG. 1).

For the development of the model, the reaction schemes below were translated into the PySB rule-based language, also shown. Rates were calculated through a parametric sweep method utilizing maximum-likelihood model-fitting procedures.

Scheme 1:

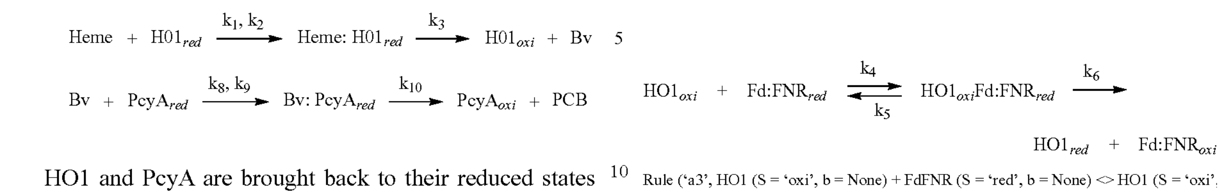

HO1 and PcyA are brought back to their reduced states through the Fd:FNR oxidative pathway:

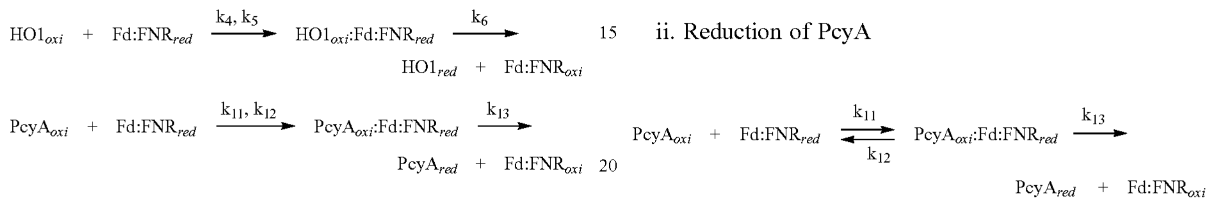

The redox of Fd:FNR is handled by ionic exchanges with NADP(H):

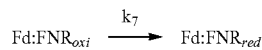

Finally, degradation of both Biliverdin and PCB were taken into account, as proposed by Miller et al., *Mol. Biosyst.* 10: 1679-1688 (2014).

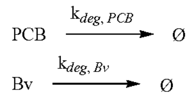

Those reactions were translated into PySB rules defining the chemical reactions between the metabolites and complexes. Those rules encompass the basic elements encoding the biochemical reactions:

a. Biliverdin Metabolism

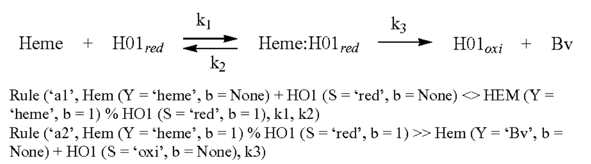

Rule ('a1', Hem (Y = 'heme', b = None) + HO1 (S = 'red', b = None) <> HEM (Y = 'heme', b = 1) % HO1 (S = 'red', b = 1), k1, k2)
Rule ('a2', Hem (Y = 'heme', b = 1) % HO1 (S = 'red', b = 1) >> Hem (Y = 'Bv', b = None) + HO1 (S = 'oxi', b = None), k3)

b. PCB Metabolism

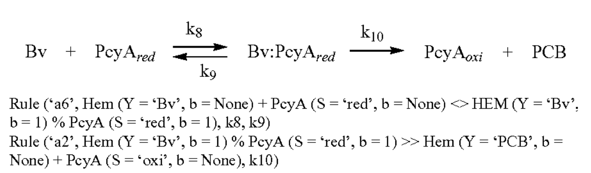

Rule ('a6', Hem (Y = 'Bv', b = None) + PcyA (S = 'red', b = None) <> HEM (Y = 'Bv', b = 1) % PcyA (S = 'red', b = 1), k8, k9)
Rule ('a2', Hem (Y = 'Bv', b = 1) % PcyA (S = 'red', b = 1) >> Hem (Y = 'PCB', b = None) + PcyA (S = 'oxi', b = None), k10)

c. Fd:FNR and Oxidative Metabolism Driven by NADP(H)

i. Reduction of HO1

Rule ('a3', HO1 (S = 'oxi', b = None) + FdFNR (S = 'red', b = None) <> HO1 (S = 'oxi', b = 1) % FdFNR (S = 'red', b = 1), k4, k5)
Rule ('a4', HO1 (S = 'oxi', b = 1) % FdFNR (S = 'red', b = 1) >> HO1 (S = 'red', b = None) + FdFNR (S = 'oxi', b = None), k6)

ii. Reduction of PcyA

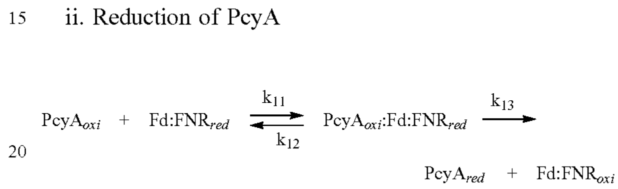

Rule ('a8', PcyA (S = 'oxi', b = None) + FdFNR (S = 'red', b = None) <> PxyA (S = 'oxi', b = 1) % FdFNR (S = 'red', b = 1), k11, k12)
Rule ('a9', PcyA (S = 'oxi', b = 1) % FdFNR (S = 'red', b = 1) >> PcyA (S = 'red', b = None) + FdFNR (S = 'oxi', b = None), k13)

iii. Fd:FNR Metabolism and Degradation Reactions

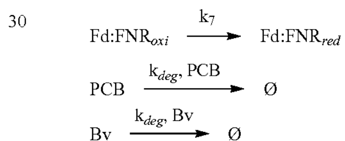

Rule ('a5', FdFNR (S = 'oxi', b = None) >> FdFNR (S = 'red', b = None), k7)
degrade (Hem (Y = 'Bv', b = None), k14)
degrade (Hem (Y = 'PCB', b = None) k15)

The PySB rules were then converted to a set of ordinary differential equations shown in Scheme 1.

Fitting the Model to Experimental Data

The model's unknown parameters were determined through a maximum likelihood approach fitted to the experimental data. Units are defined in S.I. units with concentrations as the number of metabolites for species (#molecules, or c), and parameters as bimolecular rate constants in #molecules/s$^{-1}$ (or c/s$^{-1}$).

Sum-of-Squares and Parameter Estimation

It is assumed that the system of ordinary differential equations (ODE) shown in Scheme 2 can be represented as a dynamical system given by a N-dimensional state variable $x(t)\in\mathbb{R}^N$, at time $t\in I=[t_0, t_f]$, which is the unique and differentiable solution for the initial value problem given by:

$$\dot{x}(t)=f(x(t),t,\theta)\ x(t_0)=x_0$$

As such, the ODE depends on certain parameters $\theta\in\mathbb{R}^{n}_{p}$. Also, let $Y_i$ denote the data of measurement i=1, . . . , where n represents the total amount of data. Moreover, the data $Y_i$ satisfies $Y_i=(t_i, \theta)+\sigma_i\epsilon_i$, for some function $g:\mathbb{R}^d\rightarrow\mathbb{R}^{obs}$, and d≥obs, $\sigma_i>0$ and E are independent and standard Gaussian distributed random variables. The function (–) is continuously differentiable. To estimate the parameters θ, given the initial conditions, utilizing the principle of maximum-likelihood to yield a cost function to be minimized gives:

$$\mathcal{L}(\theta)=\sum_{i=1}^{n}\frac{(Y_i-g(x(t_i;\theta)\theta))^2}{2\sigma_i^2}$$

A direct minimization of $\mathcal{L}$ with respect to θ was performed to obtain the parameters shown in Table 2, and used throughout the experiments described herein.

Implementation of Experiments

The model disclosed herein was used to gain insight into the dependencies of this pathway and to further validate the experimental results. HO1 and PcyA were assumed to be at equimolar amounts, and Fd:FNR at 1/10th of that molar concentration, following the experimental transfections (FIG. 5B). Unless stated otherwise, the following initial conditions were used. If not listed, the initial concentrations were set to zero at t=0.

[Heme](0)=10c

[$HO1_{red,oxi}$](0)=0.1c

[$Fd{:}FNR_{red,oxi}$](0)=0.01c

[$PcyA_{red,oxi}$](0)=0.1c

Experiment 1: 2E vs 4E

The experimental results show that PCB was only produced to viable levels under the presence of Fd:FNR, PcyA and HO1. To confirm this experimental result, the following parameters were modified to simulate the lack of compatible Fd:FNR, namely a "two enzyme" (2E) case, that limits the production of PCB versus the output of the pathway when all four enzymes (4E) are present. For the 2E case, [$Fd{:}FNR_{red}$](0) was set to zero (FIG. 4A).

Experiment 2: Species Specificity as Demonstrated by Different Binding Coefficients To demonstrate how the species specificity between Fd:FNR and HO/PcyA plays a pivotal role in the amount of PCB produced, a decreasing sweep was performed through the parameters $k_4$ and $k_{11}$, which control binding of HO1 and PcyA to Fd:FNR respectively. The sweeps were started at the parameter's value as described in Table 3 to 1e-2. The model fit is shown in FIG. 4C.

Experiment 3: Variable Levels of Heme

In this experiment a sweep was performed over a range of Heme concentrations, from 100, 10, 5, 1 to 0.1c. Similar experiments were performed in vitro, where different molar amounts of Heme were added to the culture medium. The model fit is shown in FIG. 4D.

Example 3 PCB Production

To develop the technology disclosed herein, PcyA and HO1 were first added into mammalian cells with or without Fd+FNR to test if exogenous Fd+FNR was required for PcyA activity. Transfected cells were lysed and PhyB protein was immunoprecipitated (IP) and washed before running on Zn-PAGE, a method that detects bilin-linked peptides (FIGS. 8*b* and 8*e*). PB+PCB ws PhyB transfected with exogenously added PCB, M2 were from cells transfected with PhyB and PcyA+HO1, M4 were from cells transfected with PhyB and mitochondrially targeted PcyA+HO1 with mitochondrially targeted Fd+FNR.

As demonstrated by FIGS. 8B and 8E, shows that PcyA+HO1 alone produce very small amount of PCB in mammalian cells and that including the Fd+FNR system in addition to HO1 and PcyA was sufficient to produce high levels of PCB.

Example 4 Mitochondria Localization

Next, it was tested to see if localizing Fd+FNR into the mitochondria along with the biosynthetic enzymes HO1+PcyA could increase bioproduction. It was clear from FIG. 2 and FIG. 8*e* that using the Fd+FNR system in the mitochondria increased production of PCB. There were only low levels of production when the Fd+FNR system was in the cytoplasm with HO1+PcyA.

Example 5 PCB Production with Various Species of Enzymes

In FIGS. 3 and 8*b*, the Fd+FNR dependent biosynthesis was tested with sets of enzymes from two cyanobacterial species of HO/PcyA/Fd/FNR, *Synechococcus* sp. strain PCC 7002 and *Thermosynechococcus elongatus*. In addition, *Arabidopsis* HY2 (Hy2) was tested with sHO1 with or without sFd+sFNR. All species tested were similarly depended on an exogenous Fd+FNR system for activity. Hy2 is a plant enzyme, so it has been shown here that an exogenous Fd+FNR system from one species can increase activity of a ferredoxin dependent enzyme from another species. In addition, Hy2 produces another near-infrared (NIR) fluorescent metabolite, phytochromobilin (PφB).

Example 6 A Gene Switch Example

Using the Fd+FNR system the biological processes can be controlled with red and NIR light. FIG. 11A is a diagram showing how the metabolite produced from the system disclosed herein can be used to control genes. When this metabolite absorbs 650 nm light, it isomerizes, leading to a conformational shift in PhyB (the protein it is covalently bound to). This leads to a more favorable interaction with PIF3. Therefore, when PhyB is bound to the DNA and PIF3 is bound to an activating domain, red light leads to the recruitment of the activation domain to any desired promoter. When far-red light (740 nm) is shined, the system reverses and the gene is turned off. FIG. 5 shows that gene activation with light is also dependent on the Fd+FNR system. Cells transfected with the gene switch along with the biosynthetic enzymes only responded to red light when the Fd+FNR system was present (2 enzymes vs 4 enzymes). This is one example of many possible ways this system can be used.

Example 7 An Example of Use for Fluorescent Imaging

Figure 6:
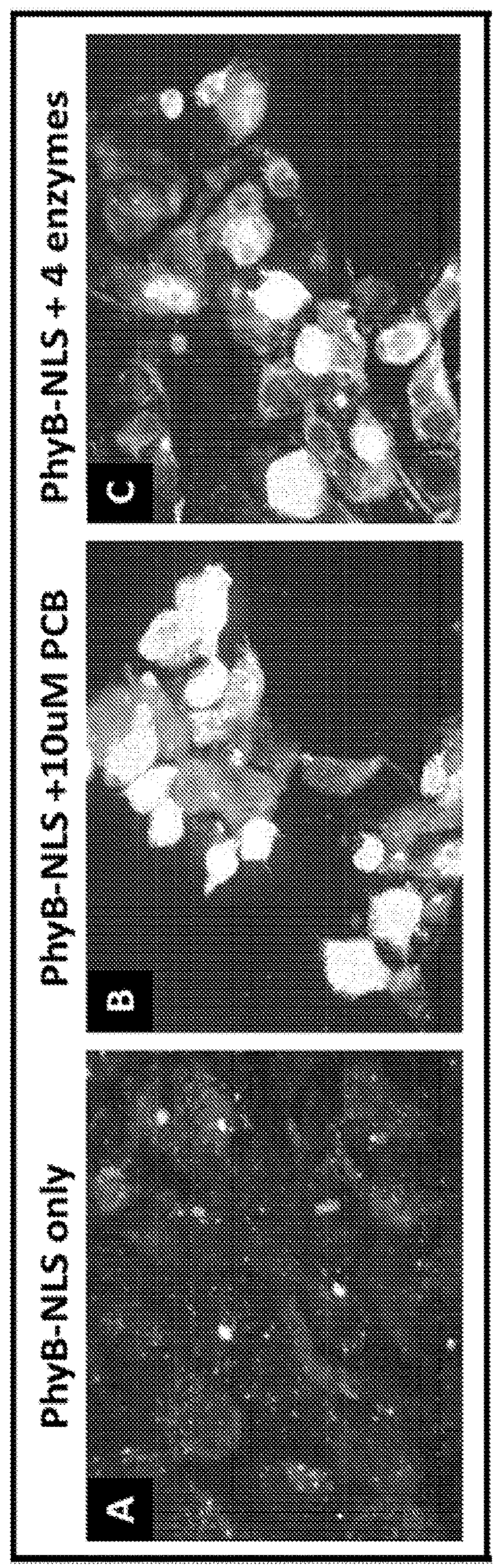
FIG. 6 shows that HO1+PcyA+Fd+FNR produces PCB for microscopy imaging.
Figure 7:
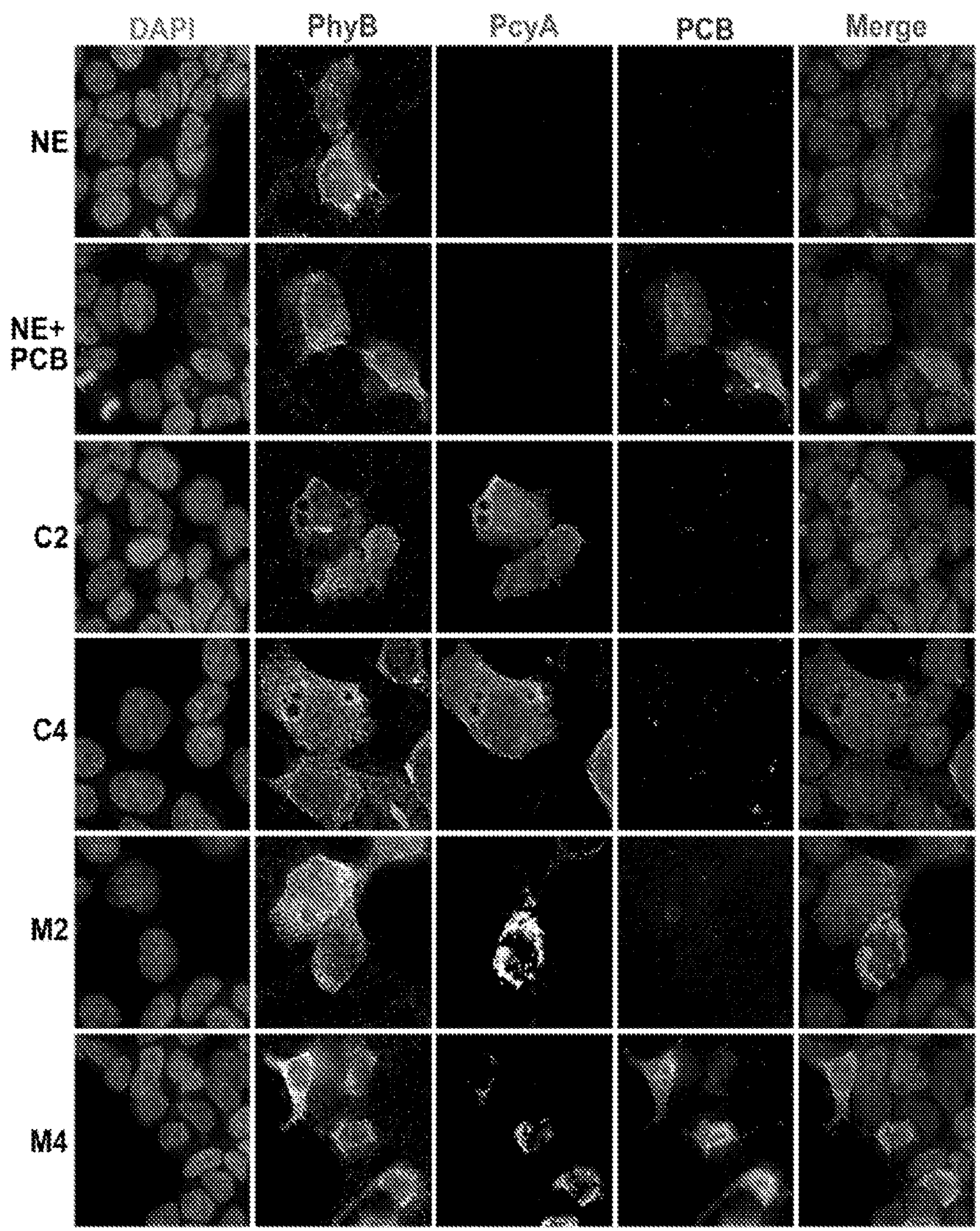
FIG. 7 shows imaging PCB production in mammalian cells. HEK293 cells were transfected with PhyB alone (NE, No Enzymes), PhyB+5 μM PCB (NE+PCB), cytoplasmic Ho1+PcyA (C2), cytoplasmic Ho1+PcyA+Fd+FNR (C4), mitochondrial Ho1+PcyA (M2), or mitochondrial Ho1+PcyA+Fd+FNR (M4). DAPI DNA stain was imaged using the DAPI channel. PhyB tagged with HA was imaged using anti-HA, PcyA tagged with FLAG was imaged using anti-FLAG. PCB was imaged directly using the Cy-5 channel. The merged image shows that cells require all four enzymes (HO1, PCYA, Fd, FNR) localized to the mitochondria for PCB production. All images were taken under the same exposure and contrast settings using a 60× (1.40NA) objective.
Figure 9:
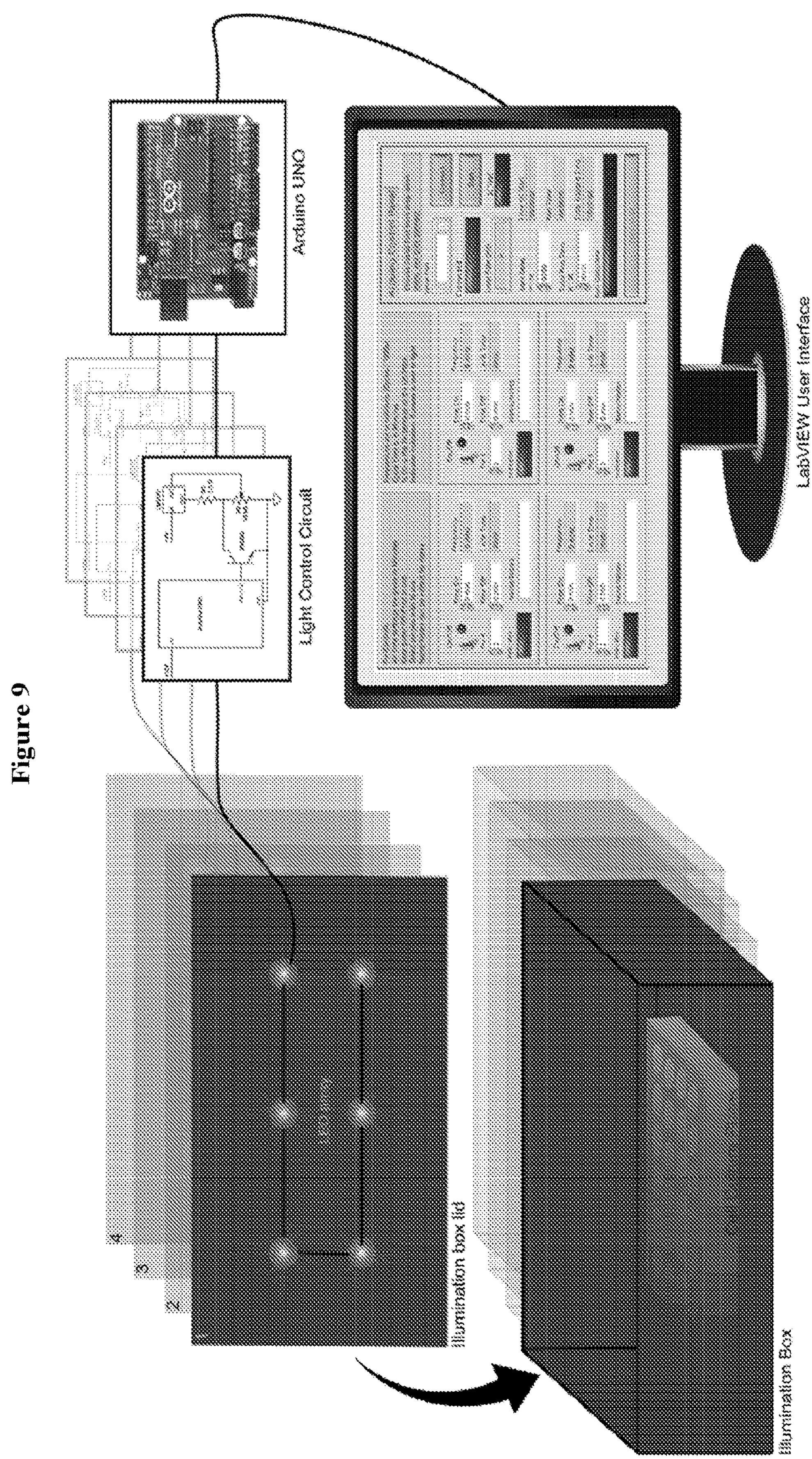
FIG. 9 illustrates an example of the illumination setup: Illumination setup consists of black boxes with LED arrays controlled via an Arduino®-driven circuitry and a LabVIEW™ user interface. The system is easily expandable to allow for the control of up to 12 boxes simultaneously. Each box can be activated at different time intervals and at different frequencies.
Figure 10:
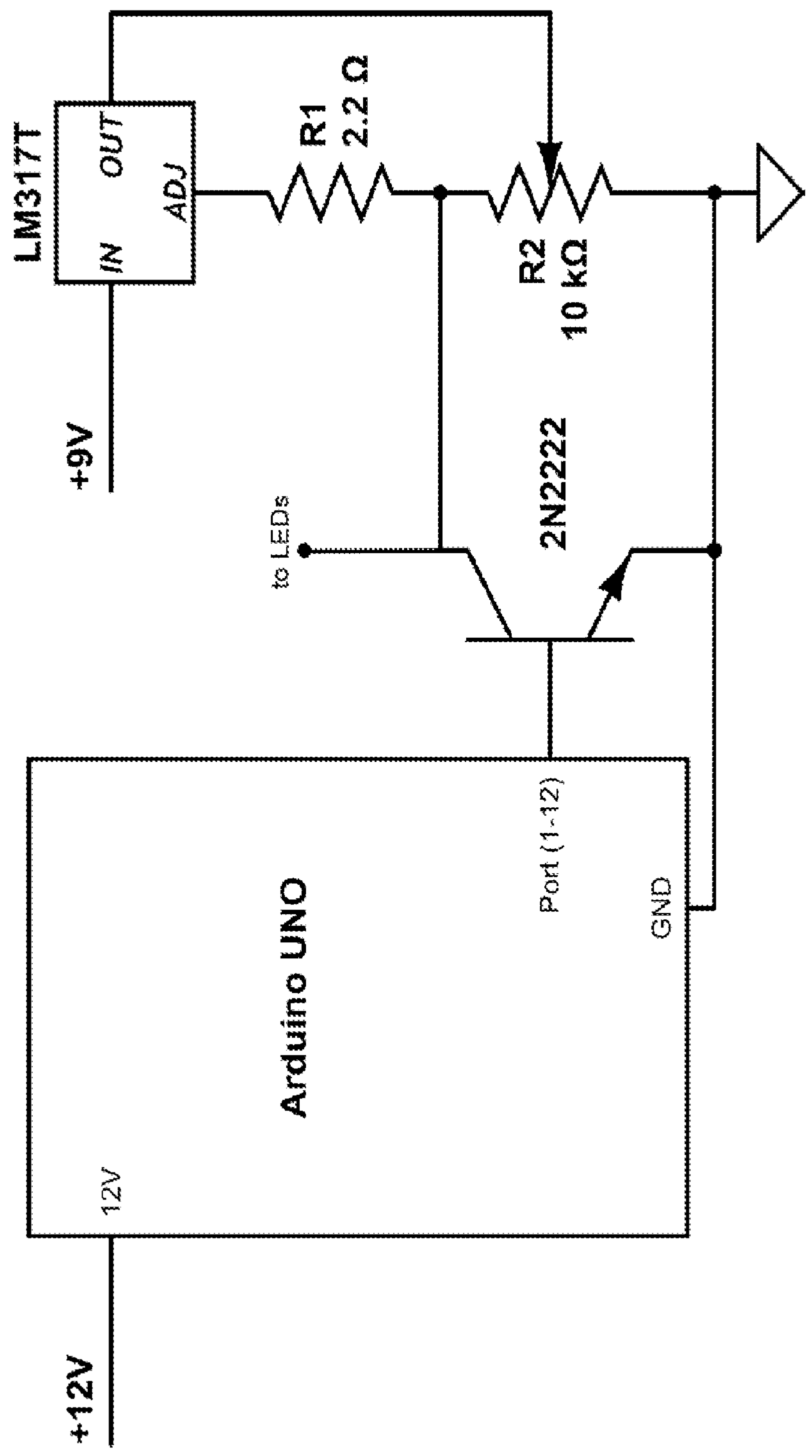
FIG. 10 illustrates an example of the Circuit Design for LED illumination: Electronic schematic of the circuit used to control the LEDs for each box, coupled with an Arduino® UNO. The circuit requires a 9 Volt voltage source, and uses simple components. A trimmer potentiometer allows for intensity and brightness control of the LEDs. This circuit can control 6 high power LEDs in series.

FIGS. 6 and 7 show the use of the system disclosed herein for fluorescent imaging. Because PCB, PφB, and related metabolites are fluorescent in the NIR optical window, they are ideal for imaging/biological control, particularly deep into tissue.

Example 8 Ferredoxin+FNR Increases Phycocyanobilin and Phytochromobilin Production in Mammalian Cells High levels of PCB (or similar bilins) are required for enabling optical control or imaging using phytochrome systems in animals. Towards overcoming this limitation, Müller et al. localized PcyA+HO1 to the mitochondria where heme and biliverdin are produced, suggesting that heme may be the rate limiting metabolite for producing PCB. However, because PcyA and HO1 are ferredoxin-dependent enzymes and mammalian ferredoxins are also localized in the mitochondria, those experiments left open the possibility that ferredoxin, and not heme, is limiting (FIG. 1).

A computational model of compartmentalized cellular expression of HO1+PcyA or HO1+PcyA+Fd+FNR was developed using coupled ordinary differential equations based on well-established enzymatic reactions (model described above), and the redox state of each enzyme and in the presence of excess heme and NADPH/NADP$^+$ was considered (FIG. 8*a*). HO1+PcyA alone produced a small burst of PCB; over time PcyA and HO1 became irreversibly oxidized (making then inactive) and PCB degradation lead to PCB depletion (open triangles). In contrast, when HO1+PcyA+Fd+FNR were all present, the Fd+FNR system had access to the cells' supply of NADPH/NADP$^+$, leading to HO1+PcyA reduction/recycling and to elevated levels of PCB (black circles). Using a Zinc-PAGE immunoprecipitation assay, the PCB production model was tested in embryonic kidney (HEK293) cells. HEK293 cells were transfected with either mitochondrial-HO1+PcyA (M2) or mitochondrial-HO1+PcyA+Fd+FNR (M4), from *Synechococcus* sp. PCC 7002 (SYNP2/sPcyA) or *Thermosynechococcus elongates* (THEEB/tPcyA) (FIG. 8*b*). HEK293 cells were transfected 24 hours after plating. Calculations are for each well. Transfected in a 6 well plate. Cells were harvested 44 hours post transfection followed by immunoprecipitation and Zn-PAGE as described above. Table 6 details the plasmids and DNAs used in the experiment.

TABLE 6

| | Plasmid | DNA mass (ng) | DNA Ratio |
|---|---|---|---|
| NE control | pPKm-105 | 125 ng | 1/20 |
| | pPKm-102 | 125 ng | 1/20 |
| | pPKm-145 | 1125 ng | 18/20 |
| M2-sPcyA | pPKm-105 | 125 ng | 1/20 |
| | pPKm-243 | 125 ng | 1/20 |
| | pPKm-234 | 1125 ng | 9/20 |
| | pPKm-145 | 1125 ng | 9/20 |
| M4-sPcyA | pPKm-105 | 125 ng | 1/20 |
| | pPKm-243 | 125 ng | 1/20 |
| | pPKm-234 | 1125 ng | 9/20 |
| | pPKm-233 | 1125 ng | 9/20 |
| M2-tPcyA | pPKm-105 | 125 ng | 1/20 |
| | pPKm-243 | 125 ng | 1/20 |
| | pPKm-232 | 1125 ng | 9/20 |
| | pPKm-145 | 1125 ng | 9/20 |
| M4-tPcyA | pPKm-105 | 125 ng | 1/20 |
| | pPKm-243 | 125 ng | 1/20 |
| | pPKm-232 | 1125 ng | 9/20 |
| | pPKm-231 | 1125 ng | 9/20 |
| M2-Hy2 | pPKm-105 | 125 ng | 1/20 |
| | pPKm-243 | 125 ng | 1/20 |
| | pPKm-235 | 1125 ng | 9/20 |
| | pPKm-145 | 1125 ng | 9/20 |
| M4-Hy2 | pPKm-105 | 125 ng | 1/20 |
| | pPKm-243 | 125 ng | 1/20 |
| | pPKm-235 | 1125 ng | 9/20 |
| | pPKm-233 | 1125 ng | 9/20 |

When HO1+PcyA were expressed alone, very low levels of PCB were detected (FIG. 8*b*, M2). However, when all four enzymes were expressed, a large increase in PCB levels was observed (FIG. 8*b*, M4). To rule out that this effect was specific to cyanobacterial enzymes, the chromophore PΦB was produced, by replacing the cyanobacterial PcyA with its plant homolog Hy2. PcyA and Hy2 showed the same Fd+FNR dependence (FIG. 8*b*). It is noteworthy that plant Hy2 (*Arabidopsis*) was used along with cyanobacterial HO1/Fd/FNR, and increased production of PΦB, a plant chromophore, was still observed. This finding shows that matching Fd+FNR to the type of ferredoxin dependent enzyme increases PCB or PΦB production in mammalian cells, even if the ferredoxin-dependent enzyme is not from the same species as the Fd-FNR system (FIG. 8*b*). Because cyanobacterial and plant Fds are similar in sequence as compared to human ferredoxins (Tables 1B and 1C), it may be possible to predict compatibility of Fd dependent enzymes with Fds across species based on sequence similarity or evolutionary origin. However, it may be that by employing entirely *Arabidopsis* enzymes, PΦB production can be further increased.

There are noteworthy advantages to using Fd+FNR's of a different species that match the species from the metabolic pathway to be introduced. First, matching the enzyme species allows for minimal perturbation of normal physiology. For example, if mammalian Fd+FNR can reduce PcyA at about 10% of the rate of the cyanobacterial Fd+FNR, then it would be necessary to express ten times as much mammalian Fd+FNR to have the same effective production rate. Second, compared to the system of a different species, overexpressing the host cell's Fd+FNR will more likely affect its metabolism.

Example 9 Ferredoxin+FNR is Rate Limiting for PCB Production

After finding the Fd+FNR dependence for chromophore production, the computational model was further developed to characterize the effects of the individual components of the pathway. First Fd+FNR compatibility with PcyA and HO1 was simulated using decreasing Fd+FNR activity in the presence of excess heme. These simulations demonstrate that PCB levels are effectively diminished with lower Fd+FNR activity levels (FIG. 8C, arrow indicates diminishing activity levels). This agrees with the in vitro findings from prior publication by Frankenberg et al., demonstrating that PcyA activity depends on the species or type of Ed used to reduce oxidized PcyA. Additionally, the two ferredoxins expressed in humans have distinct non-overlapping functions in cytochrome p450 recycling and steroid biosynthesis, confirming the relevance of the simulations for using Fd dependent enzymes from other species in mammalian cells. Next, the effect of increasing amounts of heme on PCB production was simulated. With Fd+FNR activity fixed between simulations, it was observed that increasing heme amounts lead to higher PCB production rates (FIG. 8*d*), which demonstrates how PCB production is also heme dependent.

Measuring PCB production in the presence of excess heme and/or excess Fd+FNR could reveal the rate limiting factor in mammalian cells (FIG. 8*e*). Because the endogenous ferredoxin system is localized in the mitochondria, the cytoplasmic localization of PcyA+HO1 was considered as a condition with negligible endogenous Fd+FNR activity. Using Zn-PAGE immunoprecipitation assays, FIG. 8*e* shows that expression of cytoplasmic-PcyA+HO1 (C2) alone is not sufficient to produce significant levels of PCB (lane 3 vs lane 2). In this experiment, HEK293 cells were transfected 24 hours after plating. Calculations are for each well. Transfected two of each in a 6 well plate, +/− heme. 10 μM of Heme (Frontier Scientific) was added 18 hours and 43 hours post transfection. Cells were harvested 44 hours post transfection, followed by immunoprecipitation and Zn-PAGE as described above. The plasmids and DNAs used in this experiment are detailed in Table 7.

TABLE 7

| | Plasmid | DNA mass (ng) | DNA Ratio |
|---|---|---|---|
| NE control | pPKm-105 | 125 ng | 1/20 |
| | pPKm-243 | 125 ng | 1/20 |
| | pPKm-145 | 1125 ng | 18/20 |
| C2 | pPKm-105 | 125 ng | 1/20 |
| | pPKm-243 | 125 ng | 1/20 |
| | pPKm-240 | 1125 ng | 9/20 |
| | pPKm-145 | 1125 ng | 9/20 |
| C4 | pPKm-105 | 125 ng | 1/20 |
| | pPKm-243 | 125 ng | 1/20 |
| | pPKm-240 | 1125 ng | 9/20 |
| | pPKm-241 | 1125 ng | 9/20 |
| M2 | pPKm-105 | 125 ng | 1/20 |
| | pPKm-243 | 125 ng | 1/20 |
| | pPKm-234 | 1125 ng | 9/20 |
| | pPKm-145 | 1125 ng | 9/20 |
| M4 | pPKm-105 | 125 ng | 1/20 |
| | pPKm-243 | 125 ng | 1/20 |
| | pPKm-234 | 1125 ng | 9/20 |
| | pPKm-233 | 1125 ng | 9/20 |

When cytoplasmic PcyA+HO1 was co-transfected along with cytoplasmic Fd+FNR (C4), higher, but statistically insignificant levels of PCB were detected (lane 3 vs 4, $p>0.05$). Similarly, when PcyA+HO1 alone were localized to the mitochondria (M2), low levels of PCB were detected (lane 5). However, when PcyA+HO1 and Fd+FNR were all localized to the mitochondria (M4), PCB production was significantly increased by 21.8 fold (lane 5 vs 6).

This effect is consistent with the findings from directly imaging PCB by fluorescence microscopy, as shown in FIGS. 6 and 7. In this experiment, HEK293 cells were transfected 24 h after plating on polylysine coated coverslips. 43 hours later media were changed with media+10 μM PCB (FIG. 6) media+5 μM PCB (FIG. 7) (Frontier Scientific P14137) added to the NE+PCB control. One hour later cells were rinsed in PBS and fixed in 4% Paraformaldehyde for 10 minutes. Next cells were incubated in permeabilization buffer (5% BSA+0.3% Triton™ X-100 in PBS) for 30 min, followed by primary antibodies overnight at 4° C. in antibody buffer (2% BSA+0.2% Triton™ X-100 in PBS; anti-flag mouse monoclonal 1:1000 (Sigma F3165) anti-HA rabbit polyclonal 1:500 (Santa Cruz Y-11)). Coverslips were washed in PBS followed by primary antibodies overnight at 4° C. in antibody buffer (2% BSA+0.2% Triton™ X-100 in PBS; next coverslips were washed in PBS and incubated in antibody buffer with goat anti mouse Alexa Fluor® 488 1:1000 (Thermo-Fisher A11001) goat anti rabbit Alexa Fluor® 568 1:1000 (Thermo-Fisher A11011)). Coverslips were then mounted with Fluoromount-G® (SouthernBiotech 0100-20). Images were taken using a DeltaVision® RT Deconvolution Microscope. The plasmids and DNAs used in this experiment are detailed in Table 8.

TABLE 8

| | Plasmid | DNA mass (ng) | DNA Ratio |
|---|---|---|---|
| NE control | pPKm-105 | 100 ng | 4/20 |
| | pPKm-145 | 400 ng | 16/20 |
| C2 | pPKm-105 | 100 ng | 4/20 |
| | pPKm-240 | 375 ng | 15/20 |
| | pPKm-145 | 25 ng | 1/20 |
| C4 | pPKm-105 | 100 ng | 4/20 |
| | pPKm-240 | 375 ng | 15/20 |
| | pPKm-241 | 25 ng | 1/20 |

TABLE 8-continued

| | Plasmid | DNA mass (ng) | DNA Ratio |
|---|---|---|---|
| M2 | pPKm-105 | 100 ng | 4/20 |
| | pPKm-234 | 375 ng | 15/20 |
| | pPKm-145 | 25 ng | 1/20 |
| M4 | pPKm-105 | 100 ng | 4/20 |
| | pPKm-234 | 375 ng | 15/20 |
| | pPKm-233 | 25 ng | 1/20 |

Taken together, these experiments demonstrate that the Fd+FNR system is the limiting factor in the PCB production pathway.

Next, the dependence of PCB production on heme was tested. The hypothesis was if heme is the limiting factor, then the addition of excess heme with cytoplasmic-PcyA+HO1 alone (C2) would increase PCB production (FIG. 8*e*, compare lanes 3, 8 and 9). While a faint band was visible in C2+heme (lane 9), it was indistinguishable from PhyB transfected without any enzymes (PB, lane 8). In contrast, excess heme significantly changed levels of PCB production when comparing all four cytoplasmic enzymes C4 with and without additional heme (lanes 4 and 10, $p<0.001$), and from C2+heme (lanes 9 and 10, $p<0.001$). Thus, heme becomes the limiting factor in PCB production when an excess of Fd+FNR is present in the cytoplasm. In contrast, PCB production was not influenced by excess heme when enzymes were localized to the mitochondria (M4, lanes 6 and 12). This leads to the conclusion that Fd+FNR is in fact the limiting factor in both the cytoplasm and mitochondria and that heme is secondary to the primary rate-limiting requirement of Fd+FNR for PCB production in mammalian cells.

Example 10 PCB Production in Mammalian Cells Enables Genetically Encoded PhyB-PIF Based Optogenetic Systems Adapted from Shimizu-Sato et al., *Nat. Biotechno.* 20: 1041-1044 (2002) and Müller et al., *Nucleic Acids Res.* 41: e77 (2013), several versions of the PHYB-PIF gene switch were constructed to optimize gene induction in mammalian cells (FIGS. 11*a* and 11*b*). PIF6 and PIF3 fused to the Gal4 DNA binding Domain (DBD) were first compared with PhyB fused to the β-catenin Minimal Transactivation Activating Domain (MTAD), or PIFs fused to the MTAD with PhyB fused to the DBD. With PCB added exogenously, cells illuminated with red light were compared to cells kept in the dark. Only the PIF3-MTAD with PhyB-DBD combination was red light-responsive (FIG. 11*b*). In this experiment, HEK293 cells were transfected 24 hours after plating. 15 uM of PCB (Frontier Scientific) was added 48 h after transfection. Light at 10 $\mu mol/m^2/s$ was delivered 1 h after PCB was added, and cells were illuminated for 1 minute every 4 minutes for 24 hours. 24 h after illumination, cells were lysed and stored at −20° C. until assay. The plasmids and DNAs used in this experiment are detailed in Table 9.

TABLE 9

| | Plasmid | DNA mass (ng) | DNA Ratio |
|---|---|---|---|
| P6-DBD | pPKm-102 | 1579 | 12/19 |
| | pPKm-196 | 263 | 2/19 |
| | pPKm-195 | 263 | 2/19 |
| | pPKm-118 | 263 | 2/19 |
| | pPKm-121 | 132 | 1/19 |

TABLE 9-continued

| | Plasmid | DNA mass (ng) | DNA Ratio |
|---|---|---|---|
| P3-DBD | pPKm-102 | 1579 | 12/19 |
| | pPKm-163 | 263 | 2/19 |
| | pPKm-195 | 263 | 2/19 |
| | pPKm-118 | 263 | 2/19 |
| | pPKm-121 | 132 | 1/19 |
| P6-AD | pPKm-102 | 1579 | 12/19 |
| | pPKm-105 | 263 | 2/19 |
| | pPKm-113 | 263 | 2/19 |
| | pPKm-118 | 263 | 2/19 |
| | pPKm-121 | 132 | 1/19 |
| P3-AD | pPKm-102 | 1579 | 12/19 |
| | pPKm-105 | 263 | 2/19 |
| | pPKm-112 | 263 | 2/19 |
| | pPKm-118 | 263 | 2/19 |
| | pPKm-121 | 132 | 1/19 |

Also in the presence of exogenous PCB, red light gene activation was compared using two strong synthetic activation domains, MTAD and VPR. The VPR domain activated luciferase at similar levels as MTAD (FIG. 1*c*). To find the optimal configuration for the activation domain, C-terminal and N-terminal fusions of VPR were also compared to PIF3. VPR on the C-terminus produced 2.4 fold higher luciferase activation compared to the N-terminal fusion (FIG. 5C). In this experiment, HEK293 cells were transfected 24 h after plating, followed by a medium change 24 h after transfection. For illumination, 1 μmol/m$^2$/s 1 minute pulses of red light were delivered for 24 h, starting 12 h after medium change. Cells were kept in darkness before and after illumination. Lysis was performed 72 h after transfection, and samples stored in −20° C. until assayed. The plasmids and DNAs used in this experiment are detailed in Table 10.

TABLE 10

| | Plasmid | DNA mass | DNA Ratio |
|---|---|---|---|
| P3-MTAD | pPKm-102 | 325 | 33/50 |
| | pPKm-105 | 50 | 5/50 |
| | pPKm-112 | 50 | 5/50 |
| | pPKm-118 | 50 | 5/50 |
| | pPKm-121 | 25 | 2/50 |
| P3-VPR | pPKm-102 | 325 | 33/50 |
| | pPKm-105 | 50 | 5/50 |
| | pPKm-226 | 50 | 5/50 |
| | pPKm-118 | 50 | 5/50 |
| | pPKm-121 | 25 | 2/50 |
| VPR-P3 | pPKm-102 | 325 | 33/50 |
| | pPKm-105 | 50 | 5/50 |
| | pPKm-227 | 50 | 5/50 |
| | pPKm-118 | 50 | 5/50 |
| | pPKm-121 | 25 | 2/50 |

Next, the leakiness of promoter constructs containing CMV minimal promoter with 13×TET-UAS from Müller et al. was compared to Fluc and CMV minimal promoters with 5× Gal4-UAS and to cells transfected with *Renilla* alone. The 13×TET-UAS gave a signal 172.6 fold higher than the *Renilla* only control, and both Fluc and CMV Gal4-UAS constructs had similar levels of leakiness with 16.0 and 14.2 fold activation, respectively, above the *Renilla* only control (FIG. 1*d*). In this experiment, HEK293 cells were transfected 24 h after plating, followed by a medium change 24 h after transfection. No illumination was delivered to these samples, and each 24 well plate was kept in darkness. Cells were lysed 72 h after transfection, and samples stored in −20° C. until assayed. The plasmids and DNAs used in this experiment are detailed in Table 11.

TABLE 11

| | Plasmid | DNA mass | DNA Ratio |
|---|---|---|---|
| Renilla | pPKm-102 | 480 | 48/50 |
| | pPKm-121 | 20 | 2/50 |
| TET UAS-CMV | pPKm-102 | 430 | 43/50 |
| | pMZ-802 | 50 | 5/50 |
| | pPKm-121 | 20 | 2/50 |
| G4 UAS-Fluc | pPKm-102 | 430 | 43/50 |
| | pPKm-118 | 50 | 5/50 |
| | pPKm-121 | 20 | 2/50 |
| G4 UAS-CMV | pPKm-102 | 430 | 43/50 |
| | pPKm-202 | 50 | 5/50 |
| | pPKm-121 | 20 | 2/50 |
| G4 UAS-Fluc | pPKm-102 | 20 | 2/50 |
| (Promoter + LS) | pPKm-230 | 205 | 20.5/50 |
| | pPKm-248 | 205 | 20.5/50 |
| | pPKm-118 | 50 | 5/50 |
| | pPKm-121 | 20 | 2/50 |
| G4 UAS-CMV | pPKm-102 | 20 | 2/50 |
| (Promoter + LS) | pPKm-230 | 205 | 20.5/50 |
| | pPKm-248 | 205 | 20.5/50 |
| | pPKm-202 | 50 | 5/50 |
| | pPKm-121 | 20 | 2/50 |

As an additional test, the transcription levels of the entire gene switch in the off state were measured under far-red light. The Fluc and CMV minimal promoters gave a luciferase signal 6.2 fold and 31.4 fold higher than the *Renilla* alone, respectively (FIG. 11*d*). The decrease in leakiness with the entire switch under far-red light means that for phytochrome-based gene switches, there are two useful ways to define leakiness: (1) the basal transcription rate when cells contain with reporter and control plasmids alone (UAS-Luciferase and *Renilla*, for the experiments) and (2) the basal transcription rate when cells contain the complete switch and illuminated with far-red light.

The maximal activation levels of the Gal4 UAS reporters Fluc and CMV were tested by using Gal4-VP16. The CMV minimal promoter had 3.4 fold higher the activation levels than the Fluc promoter (FIG. 11*e*). In this experiment, HEK293 cells were transfected 24 h after plating, followed by a medium change 24 h after transfection. No illumination was delivered to these samples, and each 24 well plate was kept in darkness. Cells were lysed 72 h after transfection, and samples stored in −20° C. until assayed. The plasmids and DNAs used in this experiment are detailed in Table 12.

TABLE 12

| | Plasmid | DNA mass | DNA ratio |
|---|---|---|---|
| Fluc | pPKm-102 | 380 | 38/50 |
| | pM3-VP16 | 50 | 5/50 |
| | pPKm-118 | 50 | 5/50 |
| | pPKm-121 | 20 | 2/50 |
| z,899 | pPKm-102 | 380 | 38/50 |
| | pM3-VP16 | 50 | 5/50 |
| | pPKm-202 | 50 | 5/50 |
| | pPKm-121 | 20 | 2/50 |

Together these promoter constructs allow for modularity for higher activation levels at the expense of leakiness. Depending on the application where low leakiness is essential, Fluc can be used or where high activation levels are required, the CMV minimal promoter or other UAS constructs such as the 13X-TET-UAS can be employed.

Example 11 Stoichiometry of PcyA, HO1 and Fd+FNR Affect PCB Production Levels

Considering that Fd forms stable complexes with both HO1 and PcyA, PCB production may be further optimized through enzyme stoichiometry. Separate PcyA+HO1 and Fd+FNR plasmids were transfected at different ratios, and it was observed that PCB production was highly dependent on the ratio between them (FIG. 12*a*). In this experiment, HEK293 cells were transfected 24 hours after plating. Calculations are for each well of a 6 well plate. Cells were harvested 44 hours post transfection, followed by immunoprecipitation and Zn-PAGE as described above. The plasmids and DNAs used in this experiment are detailed in Table 13.

TABLE 13

| | Plasmid | Construct | DNA mass (ng) |
|---|---|---|---|
| NE control | pPKm-105 | PhyB-DBD | 125 ng |
| | pPKm-243 | mOrange | 125 ng |
| | pPKm-145 | pSIN-emtpy vector | 1125 ng |
| (9HP:9FF) | pPKm-105 | PhyB-DBD | 125 ng |
| | pPKm-243 | mOrange | 125 ng |
| | pPKm-232 | pSIN-tHO1-P2A-tPCYA | 1125 ng |
| | pPKm-231 | pSIN-tFd-P2A-tFNR | 1125 ng |
| | pPKm-145 | pSIN-emtpy vector | 0 ng |
| (9HP:3FF) | pPKm-105 | PhyB-DBD | 125 ng |
| | pPKm-243 | mOrange | 125 ng |
| | pPKm-232 | pSIN-tHO1-P2A-tPCYA | 1125 ng |
| | pPKm-231 | pSIN-tFd-P2A-tFNR | 375 ng |
| | pPKm-145 | pSIN-emtpy vector | 750 ng |
| (9HP:1FF) | pPKm-105 | PhyB-DBD | 125 ng |
| | pPKm-243 | mOrange | 125 ng |
| | pPKm-232 | pSIN-tHO1-P2A-tPCYA | 1125 ng |
| | pPKm-231 | pSIN-tFd-P2A-tFNR | 125 ng |
| | pPKm-145 | pSIN-emtpy vector | 1000 ng |
| (17HP:1FF) | pPKm-105 | PhyB-DBD | 125 ng |
| | pPKm-243 | mOrange | 125 ng |
| | pPKm-232 | pSIN-tHO1-P2A-tPCYA | 2125 ng |
| | pPKm-231 | pSIN-tFd-P2A-tFNR | 125 ng |
| | pPKm-145 | pSIN-emtpy vector | 0 ng |

These results were confirmed through luciferase expression assays in which PCB was endogenously produced with different transfection ratios of the PcyA+HO1 and Fd+FNR plasmids. In agreement with the observed changes in PCB production, gene activation levels were also highly dependent on enzyme stoichiometry (FIG. 12*b*). In this experiment, HEK293 cells were transfected 24 h after plating, followed by a medium change 24 h after transfection. For illumination, 1 μmol/m$^2$/s 1 minute pulses of red light were delivered for 24 h, starting 12 h after medium change. Cell were kept in darkness before and after illumination. Lysis was performed 72 h after transfection, and samples stored in −20° C. until assayed. The plasmids and DNAs used in this experiment are detailed in Table 14.

TABLE 14

| | Plasmid | DNA mass | DNA ratio |
|---|---|---|---|
| 9HP:9EV (1:1 ratio HP:EV) | pPKm-102 | 425.0 | 25.5/30 |
| | pPKm-105 | 16.7 | 1/30 |
| | pPKm-112 | 16.7 | 1/30 |
| | pPKm-232 | 16.7 | 1/30 |
| | pPKm-202 | 16.7 | 1/30 |
| | pPKm-121 | 8.3 | 0.5/30 |
| 9HP:9FF (1:1 ratio HP:FF) | pPKm-102 | 408.3 | 24.5/30 |
| | pPKm-105 | 16.7 | 1/30 |
| | pPKm-112 | 16.7 | 1/30 |
| | pPKm-232 | 16.7 | 1/30 |
| | pPKm-231 | 16.7 | 1/30 |
| | pPKm-202 | 16.7 | 1/30 |
| | pPKm-121 | 8 | 0.5/30 |

TABLE 14-continued

| | Plasmid | DNA mass | DNA ratio |
|---|---|---|---|
| 17HP:1EV (17:1 ratio HP:EV) | pPKm-102 | 158.3 | 9.5/30 |
| | pPKm-105 | 16.7 | 1/30 |
| | pPKm-112 | 16.7 | 1/30 |
| | pPKm-232 | 283.3 | 17/30 |
| | pPKm-202 | 16.7 | 1/30 |
| | pPKm-121 | 8.3 | 0.5/30 |
| 17HP:1FF (17:1 ratio HP:FF) | pPKm-102 | 141.7 | 8.5/30 |
| | pPKm-105 | 16.7 | 1/30 |
| | pPKm-112 | 16.7 | 1/30 |
| | pPKm-232 | 283.3 | 17/30 |
| | pPKm-231 | 16.7 | 1/30 |
| | pPKm-202 | 16.7 | 1/30 |
| | pPKm-121 | 8.3 | 0.5/30 |

Next, a series of constructs that encoded all four enzymes on a single plasmid were generated. The original four enzyme plasmid, pPKm-245, contained all PCB biosynthetic enzymes separated by P2A sequences to achieve a 1:1:1:1 expression level of each enzyme. The results above suggested that PCB production could be further optimized by modifying the plasmid's expression stoichiometry. To this end, one of the P2A sequences was replaced with an Internal Ribosomal Entry Site (IRES) that typically gives one order of magnitude lower expression to the gene following the IRES sequence. The plasmid pPKm-244 was generated by placing an IRES between PcyA and Fd, leading to higher PcyA-HO1 levels and lower Fd+FNR levels (FIG. 11*c*). In addition, plasmid pPKm-248 containing HO1+Fd+FNR all placed after the IRES sequence was constructed, resulting in minimized heme oxygenase and Fd+FNR activity, while keeping higher levels of PcyA (FIG. 11*c*). It was found that lowering HO1 and Fd+FNR levels with the pPKm-248 plasmid produced 1.8 fold and 2.2 fold higher gene activation levels than pPKm-245 and pPKm-244 respectively (FIGS. 11*c* and 11*d*). In this experiment, HEK293 Cells were transfected 24 h after plating, followed by a medium change 24 h after transfection. For illumination, 1 μmol/m$^2$/s 1 minute pulses of red light were delivered for 24 h, starting 12 h after medium change. Cells were kept in darkness before and after illumination. Cell lysis was performed 72 h after transfection, and samples stored in −20° C. until assayed. The plasmids and DNAs used in this experiment are detailed in Table 15.

TABLE 15

| | Plasmid | DNA mass (ng) | DNA Ratio |
|---|---|---|---|
| 245 | pPKm-102 | 10 | 1/50 |
| | pPKm-230 | 225 | 22.5/50 |
| | pPKm-245 | 225 | 22.5/50 |
| | pPKm-202 | 20 | 2/50 |
| | pPKm-121 | 20 | 2/50 |
| 244 | pPKm-102 | 10 | 1/50 |
| | pPKm-230 | 225 | 22.5/50 |
| | pPKm-244 | 225 | 22.5/50 |
| | pPKm-202 | 20 | 2/50 |
| | pPKm-121 | 20 | 2/50 |
| 248 | pPKm-102 | 10 | 1/50 |
| | pPKm-230 | 225 | 22.5/50 |
| | pPKm-248 | 225 | 22.5/50 |
| | pPKm-202 | 20 | 2/50 |
| | pPKm-121 | 20 | 2/50 |

Example 12 RAGS Light Sensitivity

Several reports indicate that PCB-Phytochrome based systems are unequaled in terms of light sensitivity. RAGS's sensitivity and its reversion dynamics when expressed in mammalian cells were characterized. Interestingly, it was found that cells containing RAGS in darkness has more signal than with cells containing RAGS in the presence of far-red light (FIG. 13A), which demonstrates bistability and repressive activity of PhyB when not bound to PIF3. Thermodynamically this is expected, since some PhyB metabolites spontaneously switch to the activated state in the dark. Therefore, in darkness, the proportion of activated PhyB metabolites at steady state should be higher than when in the presence of deactivating far-red light.

Figure 13:
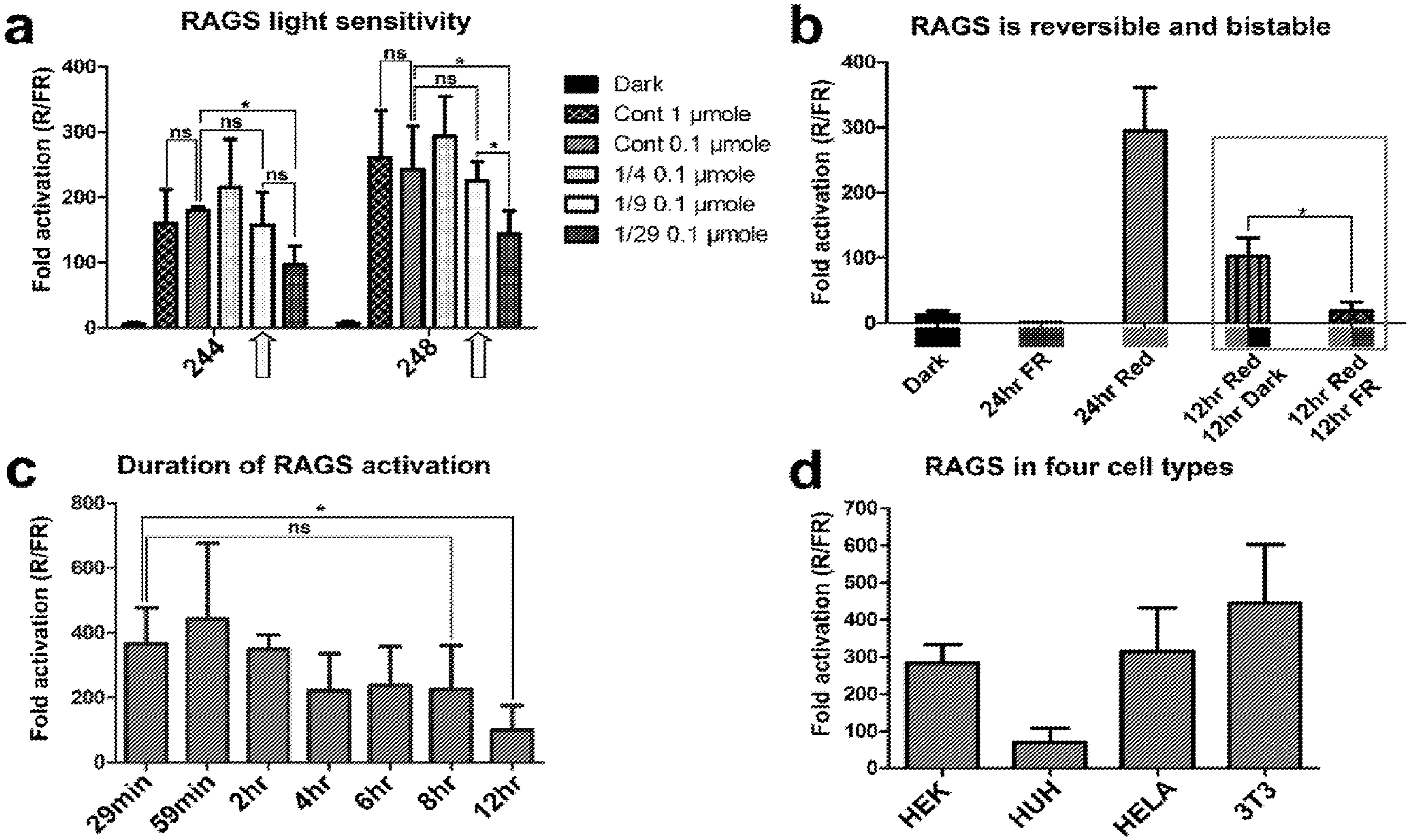
FIG. 13 demonstrates the results of RAGS gene expression assays.

In RAGS related experiments, cells were transfected 24 h after plating, followed by a medium change 24 h after transfection. In FIG. 13*a* red light at 0.1 and 1 μmol/m$^2$/s was continuously delivered or shone for 1 minute pulses every 4 minutes, 9 minutes or 29 minutes, starting 12 h after medium change for a total of 24 h. For FIG. 8*b*, cells were in darkness, illuminated with far red light, red light for 24 hours, or with 12 hours or red light followed by darkness or far-red light. For FIGS. 13*c* and 13*d*, 1 μmol/m$^2$/s 1 minute pulses of red light were delivered for 24 h, starting 12 h after medium change. Cells were kept in darkness before and after illumination. Far-red samples were kept under constant illumination starting at medium change. Cell lysis was performed 72 h after transfection, and samples stored in −20° C. until assayed. The plasmids and DNAs used in this experiment are detailed in Table 16.

TABLE 16

| | Plasmid | DNA mass (ng) | DNA Ratio |
|---|---|---|---|
| 244 (FIG. 8A) | pPKm-102 | 10 | 1/50 |
| | pPKm-230 | 225 | 22.5/50 |
| | pPKm-244 | 225 | 22.5/50 |
| | pPKm-202 | 20 | 2/50 |
| | pPKm-121 | 20 | 2/50 |
| 248 (Samples marked in FIG. 8A, and all samples in FIG. 8B-8D) | pPKm-102 | 10 | 1/50 |
| | pPKm-230 | 225 | 22.5/50 |
| | pPKm-248 | 225 | 22.5/50 |
| | pPKm-202 | 20 | 2/50 |
| | pPKm-121 | 20 | 2/50 |

Because conformational changes in PCB-bound PhyB (PhyB-PCB) from the "on" state to "off" state are bistable, the activating red light can be pulsed at different intervals to titrate down the minimal number of photons needed for maximal gene activation. Similar levels of gene activation were achieved under continuous 1 μmol/m$^2$/s and 0.1 μmol/m$^2$/s red light for 24 hours (FIG. 13*a*). This indicated that 1 μmol/m$^2$/s was saturating the system and that 0.1 μmol/m$^2$/s was greater than or equal to the saturation point (FIG. 13*a*). 0.1 μmol/m$^2$/s was also tested continuously "on", and pulsed "on" for 1 minute and "off" for 4, 9, or 29 minutes (Cont., ¼, 1/9, 1/29 respectively), (FIG. 13*a*). Continuous light at 0.1 μmol/m$^2$/s, as well as the ¼ and 1/9 conditions all had the same level of activation (FIG. 13*a*). In contrast, 0.1 μmol/m$^2$/s 1/29 had significantly lower activation than continuous light and ¼ and 1/9 conditions (FIG. 8*a*, $p<0.05$). Because the 1/9 (yellow arrow) has one tenth the number of photons as 0.1 μmol/m$^2$/s in total photon flux, it is equivalent in the number of photons to 0.01 μmol/m$^2$/s of continuous illumination or 183 nW/cm$^2$ for 660 nm light. This is 50-100× more sensitive than previously reported in mammalian and yeast cells.

Example 13 RAGS is Reversible

One hallmark of phytochrome based optogenetic switches is their conformational reversibility upon absorption of another photon of a different wavelength. While the ability for PhyB-PCB to isomerize upon red light absorption and reverse upon far-red light has been shown, whether the PhyB and PIF3 interaction was reversible by far-red light when expressed in mammalian cells has remained an open question. To address this, HEK293 cells transfected with RAGS were exposed to either 24 hours of red light, 12 hours of red light followed by 12 hours of darkness, or 12 hours of red light followed by 12 hours of far-red light (FIG. 13B). Compared to switching from red light to darkness, switching to far-red light showed significantly lower luciferase expression, indicating that the far-red light was shutting off the gene switch (grey box, $p<0.05$). This finding indicates that after red light activation, the switch remains on for some time in the darkness and can be switched off with far-red light. This suggests that the gene expression level can be titrated by timing the duration of red light or by red light followed by far-red light.

Since RAGS demonstrated bistability in mammalian cells, the minimal time to revert from the on state to the off state was measured. Cells were illuminated for 24 hours using saturating 1 μmol/m$^2$/s pulsed light with different pulse widths. If the pulse width exceeds the time to revert back to the "off" state (lowest energy state), then lower levels of gene activation should be expected. The results show that pulsing for one minute every eight hours, six hours, four hours, two hours, fifty-nine minutes and twenty-nine minutes were all equivalent to continuous illumination (FIG. 13*c*). However, pulses every 12 hours produced significantly lower gene activation than continuous light. Therefore, RAGS effectively stays "on" for more than eight hours following a one minute pulse of light.

Example 14 RAGS Performance in Several Mammalian Cell Lines

Next, how RAGS performs in different cell types was tested. HEK293, hepato cellular carcinoma (HUH-7), HeLa, and mouse fibroblasts (3T3) cells were transfected with RAGS. Using 1 μmol/m$^2$/s illumination, 1 minute pulses of red light were delivered, followed by 4 minutes of dark (abbreviated to 1/4), for a duration of 24 hours (FIG. 13*d*). RAGS activated luciferase 283 fold in HEK293 cells, 79 fold in HUH-7 cells, 315 fold in HeLa cells and 445 fold in 3T3 cells. This demonstrates a robust performance of RAGS in multiple mammalian cell types.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

The invention claimed is:

1. A system of in vivo production of a metabolite in a foreign host cell, comprising:

one or more ferredoxin dependent enzymes targeting a specific subcellular location selected from cytoplasm, mitochondria and peroxisome; and a ferredoxin (Fd)/ferredoxin-NADP+ reductase (FNR) system targeting the same specific subcellular location, wherein:

the metabolite and the one or more ferredoxin dependent enzymes are from the same species, the metabolite and the host cell are from different species, and the Fd/FNR system and the one or more ferredoxin dependent enzymes are from the same species.

2. The system of claim 1, wherein the metabolite is a bacterial metabolite, and the host cell is an animal cell or a plant cell.

3. The system of claim 1, wherein the metabolite is a plant metabolite, and the host cell is an animal cell or a bacterial cell.

4. The system of claim 1, wherein the host cell includes a bacterial cell, a plant cell, an animal cell, a vertebrate cell, and a human cell.

5. The system of claim 1, wherein the metabolite is phycocyanobilin, phytochromobilin, a steroid, ammonia, glutathione, thioredoxin or glutamate.

6. The system of claim 1, wherein the Fd/FNR system is exogenous.

7. The system of claim 1, wherein the system comprising two or more ferredoxin dependent enzymes.

8. The system of claim 1, wherein the ferredoxin dependent enzyme includes phycocyanobilin or phytochromobilin synthesis enzymes.

9. The system of claim 1, wherein the ferredoxin dependent enzyme includes HO1, PcyA and/or Hy2.

10. A method of in vivo producing a metabolite in a foreign host cell comprising:

providing to the host cell one or more ferredoxin dependent enzymes targeting a specific subcellular location selected from cytoplasm, mitochondria, and peroxisome, and a ferredoxin (Fd)/ferredoxin-NADP+ reductase (FNR) system (Fd-FNR system) targeting the same subcellular location; and culturing the host cell such that the metabolite is produced in the host cell, wherein:

the metabolite and the one or more ferredoxin dependent enzymes are from the same species, the metabolite and the host cell are from different species, and the Fd/FNR system and the one or more ferredoxin dependent enzymes are from the same species.

11. The method of claim 10, wherein the DNA encoding the one or more ferredoxin dependent enzymes is transduced or transfected into the host cell.

12. The method of claim 11, wherein the DNA of the one or more ferredoxin dependent enzymes is expressed in the host cell.

13. The method of claim 11, wherein the DNA encoding the one or more ferredoxin dependent enzymes is co-transduced or co-transfected with the DNA encoding the Fd/FNR system into the host cell.

14. The method of claim 10, wherein the metabolite is a bacterial metabolite, and the host cell is an animal cell or a plant cell.

15. The method of claim 10, wherein the metabolite is a plant metabolite, and the host cell is an animal cell or a bacterial cell.

16. The method of claim 10, wherein the host cell includes a bacterial cell, a plant cell, an animal cell, a vertebrate cell, and a human cell.

17. The method of claim 10, wherein the metabolite is phycocyanobilin, phytochromobilin, a steroid, ammonia, glutathione, thioredoxin or glutamate.

18. The method of claim 10, wherein the Fd/FNR system is exogenous.

19. The method of claim 10, wherein two or more ferredoxin dependent enzymes are provided to the host cell.

20. The method of claim 10, wherein the ferredoxin dependent enzyme includes phycocyanobilin or phytochromobilin synthesis enzymes.

21. The method of claim 10, wherein the ferredoxin dependent enzyme includes HO1, PcyA and/or Hy2.

22. A system of in vivo production of a metabolite in a foreign host cell comprising:

one or more ferredoxin dependent enzymes targeting a specific subcellular location selected from cytoplasm, mitochondria, and peroxisome, and a ferredoxin (Fd)/ferredoxin-NADP+ reductase (FNR) system (Fd-FNR system) targeting the same specific subcellular location, wherein:

the metabolite and the one or more ferredoxin dependent enzymes are from the same species, the metabolite and the host cell are from different species, the Fd/FNR system and the one or more ferredoxin dependent enzymes are from different species, and the amino acid sequence of a ferredoxin of the species of the one or more ferredoxin dependent enzymes and the amino acid sequence of a ferredoxin of the Fd/FNR species are at least 40%, at least 50%, at least 60%, at least 70%, at least 80%, at least 90%, at least 95%, or 100% identical.

23. A method of in vivo production of a metabolite in a foreign host cell comprising:

transplanting into the host cell (a) one or more ferredoxin dependent enzyme(s) targeting a specific subcellular location selected from cytoplasm, mitochondria, and peroxisome, and (b) a ferredoxin (Fd)/ferredoxin-NADP+ reductase (FNR) system (Fd-FNR system) targeting the same specific subcellular location; and culturing the transplanted host cell such that the metabolite is produced in the host cell, wherein:

the metabolite and the one or more ferredoxin dependent enzymes are from the same species, the metabolite and the host cell are from different species, the Fd/FNR system and the one or more ferredoxin dependent enzymes are from different species, and the amino acid sequence of the ferredoxin of the species of the one or more ferredoxin dependent enzymes and the amino acid sequence of the ferredoxin of the Fd/FNR species are at least 40%, at least 50%, at least 60%, at least 70%, at least 80%, at least 90%, at least 95%, or 100% identical.

* * * * *